United States Patent [19]

Monbaliu et al.

[11] 4,123,281
[45] Oct. 31, 1978

[54] PHOTOGRAPHIC SILVER HALIDE COLOR MATERIAL CONTAINING FAST-ACTING HARDENER AND 2-PYRAZOLIN-5-ONE COUPLER PRECURSORS

[75] Inventors: Marcel J. Monbaliu, Mortsel, Belgium; Hans-Heinrich Credner, Munich, Fed. Rep. of Germany; Wolfgang Himmelmann, Opladen-Lutzenkirchen, Fed. Rep. of Germany; Ernst Meier, Munich, Fed. Rep. of Germany; Gaston J. Benoy, Edegem; Raphael K. Van Poucke, Berchem, both of Belgium; Karl-Wilhelm Schranz, Odenthal-Hahnenberg, Fed. Rep. of Germany; George F. Van Veelen, Mortsel, Belgium

[73] Assignee: Agfa-Gevaert N.V., Mortsel, Belgium

[21] Appl. No.: 715,105

[22] Filed: Aug. 17, 1976

[30] Foreign Application Priority Data

Sep. 6, 1975 [DE] Fed. Rep. of Germany ....... 2539729

[51] Int. Cl.$^2$ .............................................. G03C 1/40
[52] U.S. Cl. ................................. 96/100 R; 96/56.5; 96/111
[58] Field of Search ........................ 96/100, 56.5, 111

[56] References Cited

U.S. PATENT DOCUMENTS

| 3,790,388 | 2/1974 | Shiba et al. | 96/100 |
| 3,880,665 | 4/1975 | Himmelmann | 96/111 |
| 3,898,089 | 8/1975 | Yamamoto et al. | 96/111 |

OTHER PUBLICATIONS

Oftedahl et al., Defensive Publication, T878,013, published Sep. 29, 1970.

Primary Examiner—J. Travis Brown
Attorney, Agent, or Firm—A. W. Breiner

[57] ABSTRACT

Color photographic material containing a fast-acting hardener, which acts by activating carboxyl groups, wherein said material contains a 2-pyrazolin-5-one coupler precursor corresponding to one of the following general formulae I or II:

I.
$$\begin{array}{c} R^1 \\ | \\ N \\ O=C \quad N-Z \\ | \quad | \\ Y-C = C-R \end{array}$$

II.
$$\begin{array}{c} R^1 \\ | \\ N \\ ZO-C \quad N \\ \| \quad \| \\ Y-C - C-R \end{array}$$

wherein
each of $R^1$, R and Y are substituents of the type used in 2-pyrazolin-5-one color couplers, and
Z represents acyl, alkoxycarbonyl, aryloxycarbonyl, or $$\begin{array}{c} R^1 \\ | \\ N \\ -COACO-N \quad C=O \\ | \quad | \\ R-C = C-Y \end{array}$$

or $$\begin{array}{c} R^1 \\ | \\ N \\ -COACO-O-C \quad N \\ \| \quad \| \\ Y-C - C-R \end{array}$$

in which $R^1$, R, and Y have the above-defined significance, and A represents an alkylene group or an arylene group.

8 Claims, No Drawings

PHOTOGRAPHIC SILVER HALIDE COLOR MATERIAL CONTAINING FAST-ACTING HARDENER AND 2-PYRAZOLIN-5-ONE COUPLER PRECURSORS

The invention relates to a colour photographic material, in particular to a colour photographic material containing a fast-acting hardener and a 2-pyrazolin-5-one coupler precursor.

It is known to make photographic colour images by the coupling of oxidized aromatic developing agents containing primary amino groups with colour couplers. It is common to use in this process the subtractive method of colour formation and in general cyan, magenta, and yellow are used as complementary colours to the primary colours in the formation of images dyes. It is common practice to use phenol or naphthol colour couplers for the formation of the cyan image, 2-pyrazolin-5-one couplers for the formation of the magenta image, and couplers containing a methylene group linked to one or two carbinyl groups for the formation of the yellow image.

To shorten the processing time photographic colour materials are often processed at temperatures above ambient temperature (20°–25° C). Processing temperatures above 30° C are often used nowadays. Yet, during processing of the photographic silver halide emulsions at these high temperatures the hydrophilic colloids such as gelatin, in which the silver halide, the photographic colour couplers, and further additives have been dispersed, soften and swell. In consequence of the manipulation these layers are exposed to damaging or the emulsion layer may simply get loose from the support. For these reasons the emulsion layers have to be hardened before the processing at high temperatures. The hardening can be realized by first conducting the emulsion layer through a hardening bath during the processing or by incorporating prehardeners e.g. aldehydes and halogen-containing aldehyde compounds especially formaldehyde, dialdehyde, and mucochloric acid into the photographic silver halide emulsion during its preparation.

It is particularly important for the hardening of photographic layers that maximum hardening be reached as soon as possible after drying so that the material to be hardened does not continuously change its permeability to the developer solution as is the case e.g. with mucochloric acid or formaldehyde.

The use of fast-acting hardeners for photographic purposes instead of hardeners, which act over a prolonged period, has recently become increasingly important. With the rapid progress of the hardening reaction it is possible to avoid changes in the photographic materials during storage, more particularly to avoid a continuous decrease in permeability of the photographic layers to photographic baths.

By fast-acting hardeners in this context compounds are meant, which bring about crosslinking of the gelatin within a very short time, if possible during the drying process. Maximum crosslinking is achieved within 24 h.

Very interesting fast-acting hardeners are carbodiimides such as those described in the U.S. Pat. Nos. 2,938,892 and 3,098,693, in the paper of E. Schmidt, F. Hitzler, and E. Lahde in Ber. 71, 1933 (1938), or in the paper by G. Amiard and R. Heynes in Bull. Soc. Chim. France 1360 (1956), the dihydroquinoline compounds described in the published German Patent Application No. 2,322,317, the carbamoylpyridinium compounds described in the published German Patent Applications Nos. 2,225,230 – 2,317,677, and 2,439,551, and the carbamoyloxypyridinium compounds described in the published German Patent Application 2,408,814.

A common feature of all these fast-acting hardeners is that they activate carboxyl groups. This action can be illustrated by the example of the known reaction of carbodiimides with carboxylic acids. In this reaction N-acylureas or acid anhydrides are used as activating groups. In the case of proteins containing carboxyl and amino groups, the reaction proceeds further and the activated carboxyl groups form peptide bonds with the amino groups. These compounds are therefore also known as peptide reagents (Chem. Rev. 67, (1967), pages 107–152).

Yet, the use of these fast-acting hardeners in colour photographic materials is limited, because compounds of these types often give rise to a reduced development of the magenta layers.

It is an object of the present invention to provide a colour photographic material containing fast-acting hardeners, in which the formation of the magenta image is hardly impaired or is not impaired by the quick hardening of the material before the photographic processing.

According to the invention a colour photographic material is provided, which is hardened by fast-acting hardeners activating carboxyl groups, characterized in that the material contains a coupler precursor, which in alkaline developer medium is converted into the 2-pyrazolin-5-one coupler, which is at disposal for the coupling.

The 2-pyrazolin-5-one coupler precursors used according to the invention together with the fast-acting hardeners activating carboxyl groups correspond to one of the following general formulae I and II:

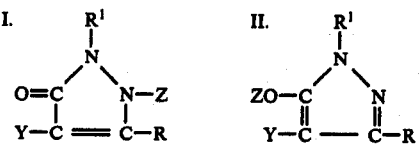

in which represent:

R¹ a substituent of the commonly used type in colour couplers of the 2-pyrazolin-5-one class e.g. an alkyl group, especially an alkyl group having 1 to 22 carbon atoms preferably 1 to 5 carbon atoms, which may be substituted, e.g. 2,2,2-trifluoroethyl, cyanoethyl, a benzyl group including a substituted benzyl group e.g. chlorobenzyl etc., a heterocyclic group e.g. furanyl, 2-benzothiazolyl, or an aryl group, especially a phenyl group, which may carry one or more substituents such as e.g. alkyl e.g. methyl, halogen e.g. chloro and bromo, sulpho, alkoxy e.g. methoxy, aryloxy e.g. phenoxy, alkylsulphonyl e.g. methylsulphonyl, alkylthio e.g. methylthio, carbalkoxy, haloalkoxy, haloalkylthio, haloalkylsulphonyl, sulphamyl or carbamyl including substituted sulphamyl or carbamyl, cyano, nitro, etc.; representative examples for substituted phenyl are e.g. 2-chlorophenyl, 2-bromophenyl, 2,6-dichlorophenyl, 2,4,6-trichlorophenyl, 3,5-dibromophenyl, 4-chlorophenyl, 2-cyanophenyl, 4-cyanophenyl, 4-nitrophenyl, 2-nitrophenyl, 4-methylphenyl, 2,6-dimethylphenyl, 4-butylphenyl, 2-trifluoromethylphenyl, 2-ethoxyphenyl, 2-butoxyphenyl, 4-phenoxyphenyl, N-methylbenzamidophenyl, N,N-diphenylcarbamylphenyl, N-methyl-N-octadecylcarbamylphenyl, Phenyl-N-methylsulphonamidophenyl, 2-methyl-5-nitrophenyl, 2-chloro-5-cyanophenyl, 5-chloro-2-methylphenyl, 2,6-dichloro-4-methoxyphenyl, 2,4-dichloro-6-methylphenyl, 2,6-dichloro-4-nitrophenyl, 2-chloro-4,6-dimethylphenyl, 2,6-dichloro-4-methylsulphonylphenyl, etc. an alkyl group, especially an alkyl group having 1 to 22 carbon atoms, which may be substituted; an aryl group including a substituted aryl group; preferably either anilino including substituted anilino, e.g. anilino with one or more common substituents e.g. alkyl, alkoxy, alkylthio, aryloxy, halogen e.g. chloro, nitro, cyano, sulpho, amino and substituted amino, e.g. carbonamido or sulphonamido, sulphamyl or carbamyl including substituted sulphanyl or carbanyl etc. or an acylamino group including a substituted acylamino group derived from carboxylic or sulphonic acids e.g. acetamido, propionamido, acrylamido, methacrylamido, palmitamido, butyl-sulphonamido, docosylsulphonamido, phenylethylsulphonamido, benzamido or phenylsulphonamido including benzamido and phenylsulphonamido carrying one or more common substituents e.g. halogen e.g. chloro and bromo, alkyl e.g. methyl, alkoxy e.g. methoxy, ethoxy, hexadecyloxy, aroxy e.g. phenoxy and substituted phenoxy, carbonamido e.g. acetamido, phenoxyacetamido, α-(2,4-di-t-amylphenoxy) acetamido etc., Y hydrogen, a group that can be split off during colour development e.g. a group used as substituent in the 4-position of one of the known coloured or colourless dye-forming 2-pyrazolin-5-one couplers, and which are split off during colour development e.g. halogen e.g. chloro, a sulpho group in acid or salt form, alkoxy e.g. methoxy, an aryloxy group e.g. phenoxy, an acyloxy group, an alkylthio or an arylthio group, e.g. phenylthio, a heterocyclic thio group e.g. 1-phenyl-5-tetrazolylthio, 2-benzothiazolylthio, and 2-benzimidazolylthio, an arylazo group e.g. phenylazo, chlorophenylazo, and methoxyphenylazo, or a benzotriazolyl group, or a group that cannot be split off during colour development such as in the known 2-pyrazolin-5-one competing couplers e.g. an alkyl group e.g. methyl;

Z (1) an acyl group deriving from an organic carboxylic acid e.g. an acyl group deriving from saturated or unsaturated aliphatic, cycloaliphatic, aliphatic-aromatic, aromatic or heterocyclic carboxylic acids, e.g. acetyl, propionyl, palmitoyl, alkoxyacetyl e.g. methoxyacetyl and ethoxyacetyl, aryloxyacetyl e.g. phenoxyacetal, β-carboxypropionyl, chloroacetyl, benzoyl, chlorobenzoyl and thienoyl or the group

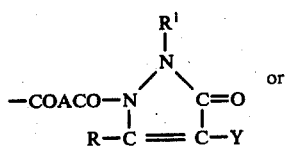

or

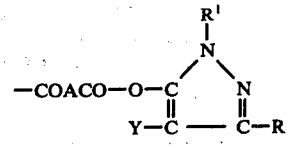

in which $R^1$, R, and Y have the above described significance, and A represents an alkylene group e.g. ethylene or an arylene group e.g. phenylene or (2) an alkoxycarbonyl or aryloxycarbonyl group, which may carry substituents e.g. methoxycarbonyl, ethoxycarbonyl, trichloroethoxycarbonyl, benzyloxycarbonyl, phenoxycarbonyl, sulphophenoxycarbonyl, alkoxycarbonylphenoxycarbonyl, etc.

The 2-pyrazolin-5-one coupler precursors according to the generalformulae I and II can be prepared from the corresponding known 2-pyrazolin-5-one couplers by reaction with an organic carboxylic acid halide in particular carboxylic acid chloride or with a chloroformiate.

Details concerning their preparation can be found in the following American Patent Specifications 2,476,986 — 2,476,987 — 2,476,988 — 2,575,182 — 2,706,685, and 2,867,748, in the U.K. patent specification No. 1,057,436, and the published German Patent Applications Nos. 2,424,134 and 2,523,882, unless they will be described hereinafter.

In the production of appropriate photographic multilayer materials containing colour couplers for the formation of separation images in the differently sensitized silver halide emulsion layers or containing competing couplers, these couplers have to be incorporated in non-diffusing form into the hydrophilic silver halide emulsion layers or into water-permeable adjacent layers.

In order to reduce the diffusion tendency of the coupler precursors in the photographic colloid layers these compounds may be provided with a ballasting group in the 1- or 3-position. For this purpose groups $R^1$ and R may e.g. represent or contain an acyclic aliphatic carbon group having 5 to 20 carbon atoms, wherein these groups may be linked via bivalent bridging elements e.g. sulphur, sulphonyl, —NHCO—, —CON(R)—, —SO$_2$N(R)—, wherein R=H or alkyl, —NHSO$_2$— or —N(alkyl)—, to the possibly aromatic groups $R^1$and/or R.

Another valuable method for the non-diffusing incorporation of coupler precursors into photographic colloid layers consists in their use in polymeric form, which can be obtained, e.g. by copolymerization of monomeric couplers according to the above formula I or II, which in the 3-position contain an ethylenic group, e.g. the group

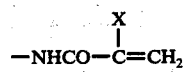

in which X represents hydrogen, halogen, a $C_1$–$C_5$ alkyl group e.g. methyl, an aralkyl group or an aryl group, with one or more non-colour forming monomers containing at least one ethylenic group.

Examples of 2-pyrazolin-5-one coupler precursors according to formulae I and II are the following:

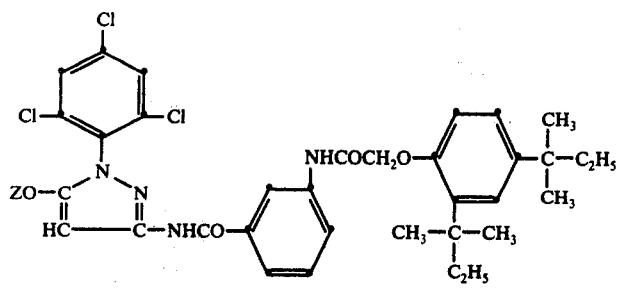
1. Z = CH$_3$CO—
2. Z = C$_2$H$_5$OCO—
3. Z = C$_6$H$_5$OCO—
4. Z = C$_6$H$_5$CO—
5. Z = C$_6$H$_5$OCH$_2$CO—
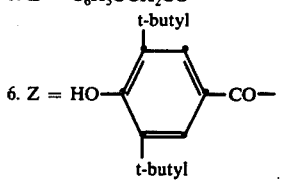
6. Z = 
7. CH$_3$OCH$_2$CO—
8. 4-FSO$_2$C$_6$H$_4$OCH$_2$CO—
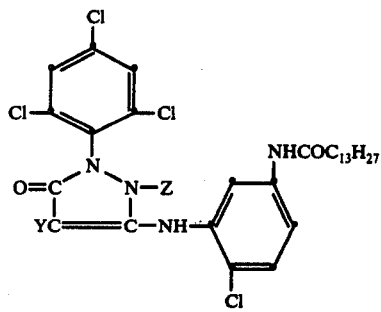
9. Z = C$_6$H$_5$OCO—      Y = H
10. Z = C$_2$H$_5$OCO—     Y = H
11. Z = C$_2$H$_5$OCO—     Y = Cl
12. Z = CH$_3$CO—          Y = H
13. Z = 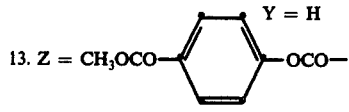   Y = H
14. Z = (HO-t-butyl-t-butyl-phenyl)CO   Y = H
15. 4FSO$_2$C$_6$H$_4$OCO—   Y = H
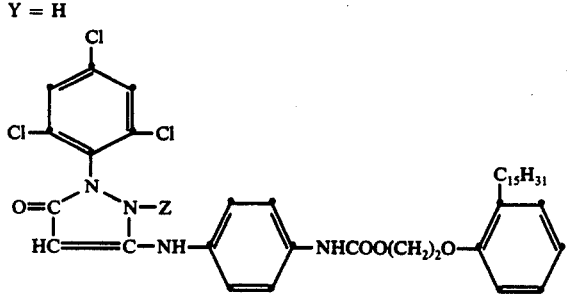
16. Z = C$_6$H$_5$OCO—
17. Z = 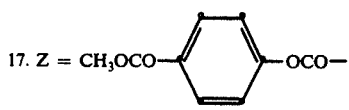

-continued
18. 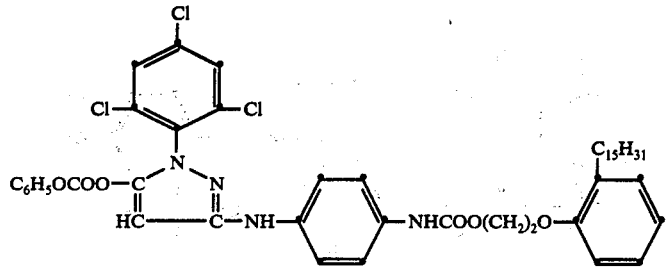
19. 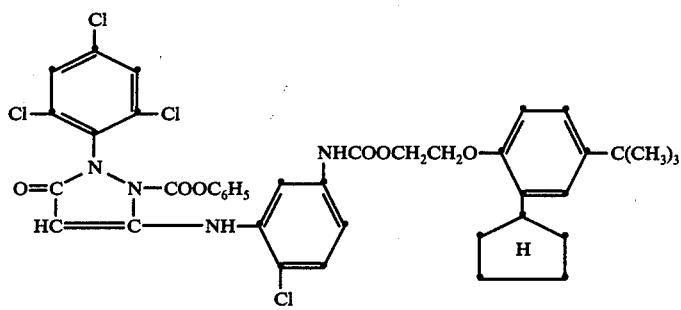
20. 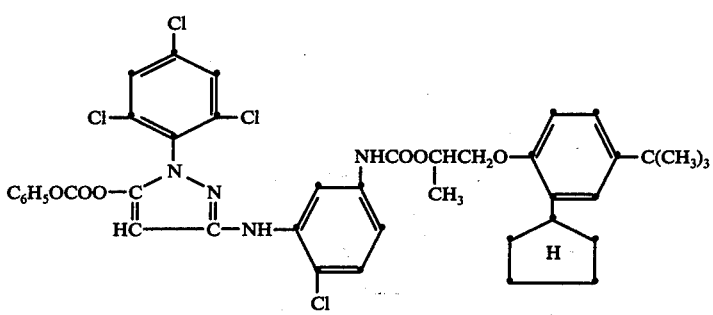
21. 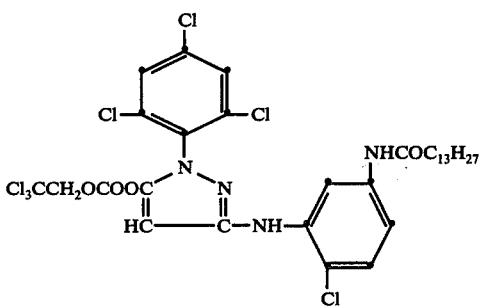
22. 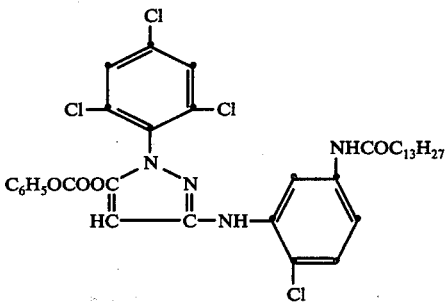
23. 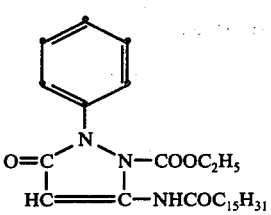

-continued
24. 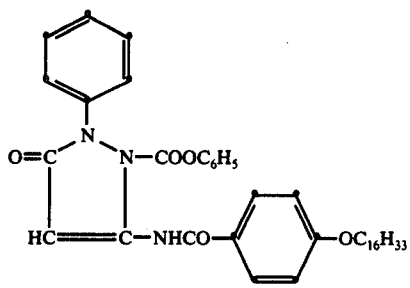
25. 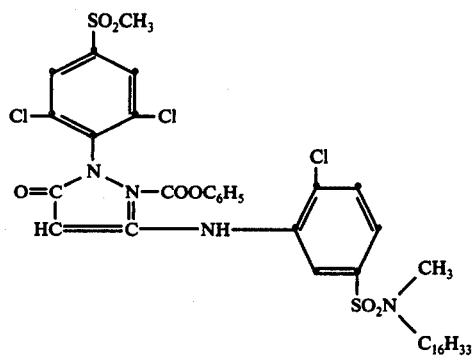
26. 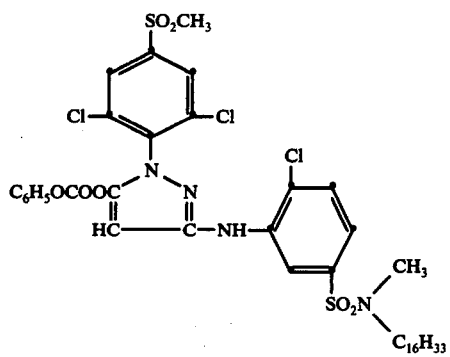
27. 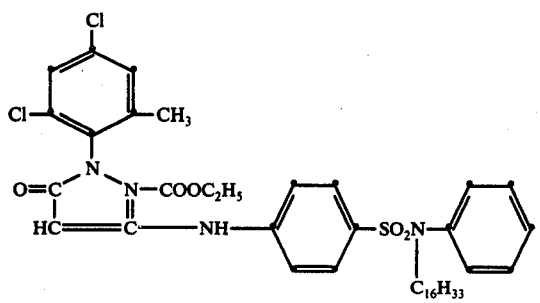
28. 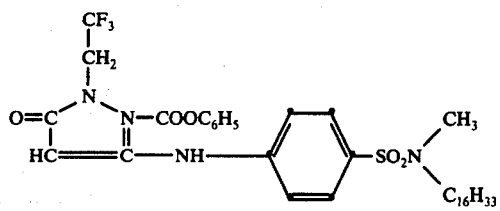

29. 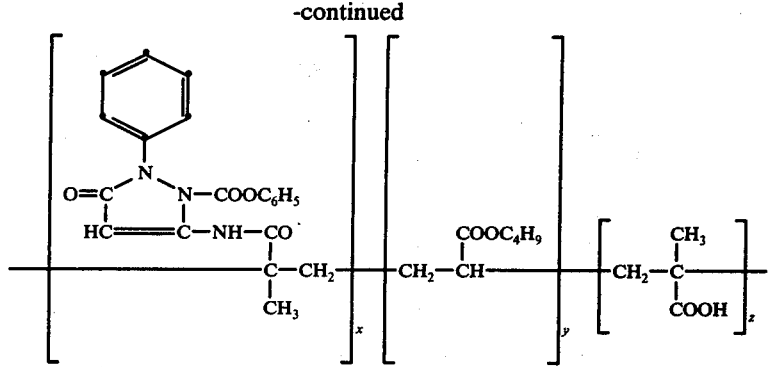

30. 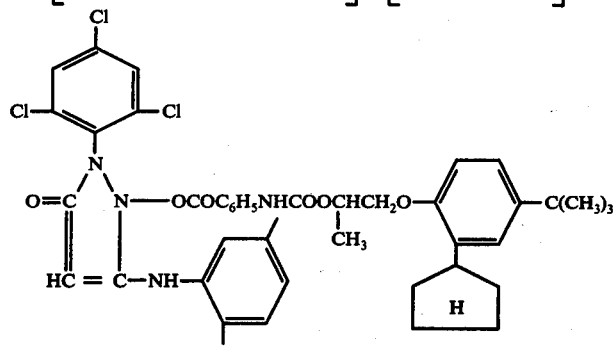

31. 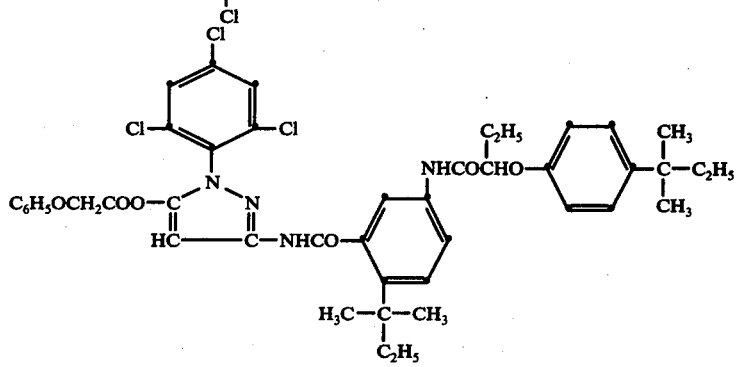

Because of the inactive methylene group the coupler precursors according to the general formulae I and II can take part in undesired side-reactions with the fast-acting hardener activating carboxyl groups during the preparation and the storage of the colour material. This results in a reduced hardening and in smaller amounts of coupler available for coupling with the oxidized developing agent, and consequently in a reduced colour density, which would result in staining. The coupling reaction in alkaline medium is more vigorous, however, than these side-reactions and leads to the splitting off of the 2- or 5-acyl group resulting in the formation of 2-pyrazolin-5-coupler, which is at the disposal for coupling.

The 2-acyl-3-pyrazolin-5-one compounds for use according to the invention are prepared by reaction of the corresponding 2-pyrazolin-5-ones as starting product with an organic carboxylic acid halide in particular a carboxylic acid chloride or with a chloroformiate.

The reaction is carried out preferably in an anhydrous inert organic solvent e.g. nitrobenzene, nitromethane, tetrahydrothiophene-1,1-dioxide, acetonitrile, dioxan or especially in halogenated aliphatic hydrocarbons such as dichloromethane, 1,2-dichloroethane or carbon tetrachloride.

When in the preparation of the compounds according to the invention chloroformiate is used as acylating agent, the inert solvent may be replaced wholly or partially by excess chloroformiate. The reaction of the 2-pyrazolin-5-one is performed in the presence of a Friedel-Crafts catalyst, especially a metal halide such as aluminium halide, e.g. aluminium chloride and a basic heterocyclic nitrogen-containing condensating agent such as pyridine or a derivative thereof, e.g. lutidine or picoline at temperatures below 20° C, especially between −20° C and +10° C.

When, however, 3-anilino-2-pyrazolin-5-one is used as starting product and chloroformiate as acylating agent, it is sufficient to reflux the reagents in the inert solvent.

In the case of an unsubstituted amino group in the 3-position of 2-pyrazolin-5-one the reaction is preferably carried out between −20° C and 0° C, since in this temperature range there is only acylated in the 2-position, whereas at higher temperatures the 3-acylaminopyrazolone compound is formed (see the U.S. Pat. Nos. 3,325,482 and 3,846,444). In order to prepare the 2-acyl-3-acylamino-3-pyrazolin-5-one compounds according to the invention the 2-acyl-3-amino-3-pyrazolin-5-one is prepared first by acylation in the presence of a Friedel-Crafts-metal halide and a basic condensation agent at relatively low temperatures preferably below 0° C. The resulting product is then acylated in the 3-position according to known methods e.g. in the presence of a Friedel-Crafts-metal halide, in an anhydrous inert solvent such as those defined hereinbefore.

If Friedel-Crafts-metal halides are used for the preparation of the compounds according to the invention the halide is taken in almost equimolar amounts in respect of the amount of the 2-pyrazolin-5-one. However, to simplify the solution of the pyrazolin-5-one the metal halide may be used in excess with a molar proportion of approximately 1:1.5.

It is obvious that preferred substituents can be introduced into the groups $R^1$, R, and Y according to known chemical methods subsequent to the 2-acylation.

The 3-anilino-5-pyrazolylalkylcarbonates or -arylcarbonates to be used according to the invention are prepared by reaction of a 3-anilino-2-pyrazolin-5-one with a chloroformiate at a temperature below −20° C, preferably between −40° C and −80° C, in the presence of an inert organic strong base with a pKb-value of at most 5, e.g. an aliphatic tertiary amine such as triethylamine.

The reaction of the 3-anilino-2-pyrazolin-5-one colour coupler with the chloroformiate is carried out preferably in an organic solvent e.g. dichloromethane, acetonitrile, dioxan etc. The molar proportion between pyrazolinone and ester advantageously ranges between 1:1 and 1:5, the molar proportion between pyrazolinone and organic base ranging between 1:1 and 1:5 as well.

It is obvious that preferred substituents can be introduced into the groups $R^1$, R, and Y prior or subsequent to the conversion according to known chemical methods.

The structures of the compounds are determined by IR and NMR-spectrometry. The alkyl- and aryl-5-pyrazolyl carbonates differ from the 2-aryloxycarbonyl- or 2-alkoxycarbonyl-3-pyrazolin-5-ones by
(1) the IR-absorption frequency (in dichloromethane) of the carbonyl group i.e. 5.70–5.80 λm in the case of the 2-acylated compounds and 5.55–5.60 μm in the case of the 5-acylated compounds and
(2) the chemical shift (in CDCl$_3$) of the C-proton of the 4-position, i.e. in the case of 2-acylated compounds less than 6 ppm and in the case of 5-acylated compounds more than 6 ppm as compared with tetraethylsilane.

The four conceivable isomeric structures (acylation in the 2-, 3-, 4-, or 5-position) differ by their IR- and NMR-spectra. The 2- and 5-acylated compounds contain no enolizable active proton in the 4-position.

The following examples illustrate the preparation of the compounds according to the invention.

Compound 9:
1-(2,4,6-trichlorophenyl)-2-phenoxycarbonyl-3-(2-chloro-5-myristoylamino-anilino)-3-pyrazolin-5-one A solution of 30.7 g (0.05 mole) of 1-(2,4,6-trichlorophenyl)-3-(2-chloro-5-myristoylamino-anilino)-2-pyrazolin-5-one and 15.6 g (0.1 mole) of phenyl chloroformiate in 100 ml of acetonitrile are refluxed for 4 h. The solution is poured out in water and the separated oil is stirred first with water and next with methanol. The precipitate is recrystallized from ethanol.
Yield: 20 g (54%). Melting point: 124° C.
Structural analysis
IR $\gamma_{CO}$ 5.73 μm NMR $\delta_{-CH=}$ 5.82 ppm Compound 13:
1-(2,4,6-trichlorophenyl)-2-(4-methoxycarbonyl-phenoxycarbonyl)-3-(2-chloro-5-myristoylamino-anilino)-3-pyrazolin-5-one A solution of 24.5 g (0.04 mole) of 1-(2,4,6-trichlorophenyl)-3-(2-chloro-5-myristoylamino-anilino)-2-pyrazolin-5-one and 17.16 g (0.8 mole) of methoxycarbonylphenyl chloroformiate (Chem.Ztg. 390 (1886)) in 100 ml of dry dichloromethane is refluxed for 8 h. The solution is concentrated by evaporation and the white precipitate is recrystallized from methanol.
Yield: 27 g (69%). Melting point: 156° C.
Structural analysis
IR $\gamma_{CO}$ 5.72 μm NMR $\delta_{-CH=}$ 5.85 ppm Compound 10:
1-(2,4,6-trichlorophenyl)-2-ethoxycarbonyl-3-(2-chloro-5-myristoylamino-anilino)-3-pyrazolin-5-one (a) Analogously to compound 13 16 g (51%) of the abovementioned compound melting at 136° C are obtained from 30.7 g (0.05 mole) of the 2-pyrazolin-5-one and 10.85 g (0.1 mole) of ethylchloroformiate.
Structural analysis
IR $\gamma_{CO}$ 5.76 μm NMR $\delta_{-CH=}$ 5.65 ppm (b) 12 ml (0.15 mole) of pyridine are added at 10° C to a solution of 30.7 g (0.05 mole) of the corresponding 2-pyrazolin-5-one, and 150 ml of acetonitrile. 5.25 ml (0.055 mole) of ethylchloroformiate are added dropwise in 5 min at 5°–10° C to the resulting suspension. 200 ml of dimethylformamide are then added to the solution of the reaction mixture. The mixture is stirred for 1 h and then poured out into a mixture of 100 ml of methanol and 100 ml of 1N aqueous hydrochloric acid. The precipitate is sucked off and recrystallized from methanol.
Yield: 26 g (76%). Melting point: 137° C.

Compound 19:
1-(2,4,6-trichlorophenyl)-2-phenoxycarbonyl-3-{2-chloro-5-[β-(2-cyclopentyl-4-t-butyl-phenoxy)-ethoxycarbonylamino]-anilino}-3-pyrazolin-5-one Analogously to compound 13 18 g (44%) of the abovementioned compound melting at 154° C are obtained from 34.6 g (0.05 mole) of the corresponding 2-pyrazolin-5-one and 15.6 g (0.01 mole) of phenylchloroformiate after recrystallization from acetonitrile.
Structural analysis
IR $\gamma_{CO}$ 5.74 μ NMRμ $_{-CH=}$ 5.80 ppm Compound 27:
1-(2-methyl-4,6-dichlorophenyl)-2-ethoxycarbonyl-3-[4-(N-phenyl-N-n-hexadecylsulfamyl)-anilino]-3-pyrazolin-5-one A solution of 28.5 g (0.04 mole) of the corresponding 2-pyrazolin-5-one and 10.85 g (0.1 mole) of ethylchloroformiate in 80 ml of acetonitrile is refluxed for 6 h. The solution is poured out in water and the resulting oil is separated and dissolved in diethylether. Hexan is added to the dried solution and the white precipitate obtained is collected. Yield: 15 g (39%). Melting point: 85° C.
Structural analysis
IR $\gamma_{CO}$ 5.77 μ NMR $\delta_{-CH=}$ 5.48 ppm Compound 20:
1-(2,4,6-trichlorophenyl-3-{2-chloro-5-[α-methyl-β-(2-cyclopentyl-4-t-butyl-phenoxy)-ethoxycarbonyl-amino]-anilino}-5-pyrazolyl-phenylcarbonate 11.75 g (0.075 mole) of phenylchloroformiate are added dropwise in 15 min to a solution cooled to −60° C of 35.3 g (0.05 mole) of the corresponding 3-anilino-2-pyrazolin-5-one and 10.35 ml (0.75 mole) of triethylamine in 100 ml of dichloromethane, so that the temperature remains below −60° C. After 15 min 0.1 N hydrochloride acid is poured first on the dichloromethane layer and subsequently it is washed with ice-water until free from acid. After drying the solvent is removed by evaporation and the residue is stirred with hexan. The precipitate is filtered off.

Yield: 24 g (58%). Melting point: 70° C.
Structural analysis
IR $\gamma_{CO}$ 5.56 μ NMR $\delta_{CH=}$ 6.28 ppm Particularly suited fast-acting hardeners belong to one of the groups of compounds corresponding to the following general formulae A to E.

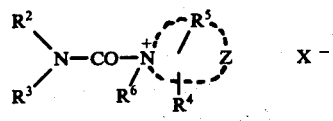

in which
- $R^2$ represents an alkyl group including a substituted alkyl group, preferably an alkyl group having 1 to 3 carbon atoms, an aryl group, which may be substituted with a lower alkyl group or with halogen, e.g. phenyl, which may be substituted with methyl, ethyl, or propyl, chlorine or bromine, or an aralkyl group e.g. benzyl, which may be substituted in the same way as the aryl group,
- $R^3$ may represent the same group as $R^2$ or a double-bonded alkylene, arylene, aralkylene or alkyl-arylalkyl group, any of which may be substituted, e.g. an ethylene, propylene, phenylene or xylylene group, which is connected through its second bond to another carbamoyl ammonium group of the formula

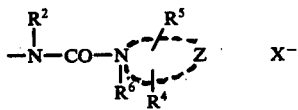

or,
- $R^2$ and $R^3$ may together represent the atoms required to complete a piperidine, piperazine, or morpholine ring, which ring may be substituted, e.g. with an alkyl group having 1 to 3 carbon atoms or with halogen such as chlorine or bromine,
- $R^4$ represents hydrogen, an alkyl group having 1 to 3 carbon atoms or the group $+A+_\alpha$, in which A represents a vinyl group of a polymerized vinyl compound or a copolymer with other copolymerizable monomers and β denotes a number such that the molecular weight of the compound is greater than 1000,
- $R^5$ represents hydrogen, alkyl having 1 to 3 carbon atoms, or, if Z represents the atoms required to complete a pyridinium ring and $R^4$ is absent, $R^5$ represents one of the following groups:

| | |
|---|---|
| $-NR^7-CO-R^8$ | $R^7$ = H, Alkyl $(C_1-C_4)$ <br> $R^8$ = H, Alkyl $(C_1-C_4)$, $NR^9R^{10}$ <br> $R^9$, $R^{10}$ = (same or different) H, Alkyl $(C_1-C_4)$ |
| $-(CH_2)_m-NR^{11}R^{12}$ | $R^{11}$ = $-CO-R^{13}$ <br> $R^{12}$ = H, Alkyl $(C_1-C_4)$ <br> $R^{13}$ = H, Alkyl $(C_1-C_4)$, $NR^{14}R^{15}$ <br> $R^{14}$ = Alkyl $(C_1-C_4)$, Aryl <br> $R^{15}$ = H, Alkyl, Aryl <br> m = 1-3 |
| $-(CH_2)_n-CONR^{16}R^{17}$ | $R^{16}$ = H, Alkyl $(C_1-C_4)$, Aryl <br> $R^{17}$ = H, Alkyl $(C_1-C_4)$ oder <br> $R^{16}$ and $R^{17}$ together represent the atoms required to complete a 5- or 6-membered aliphatic ring <br> n = 0-3 |
| $-(CH_2)_p-CH-R^{18}$ <br> $\quad\quad\quad\;\;\;\;\;\;\;\;Y$ <br> $\quad\quad\quad\;\;\;\;\;\;\;\;R^{19}$ | $R^{18}$ = H, Alkyl $(C_1-C_4)$, which may be substituted by halogen <br> Y = $-O-$, $-NR^{20}-$ <br> $R^{19}$ = H, Alkyl, $-CO-R^{21}$, $-CO-NHR^{22}$ <br> $R^{20}$, $R^{21}$, $R^{22}$ = (same or different) H, Alkyl $(C_1-C_4)$ <br> p = 2-3 |

$R^6$ represents an alkyl, aryl, or aralkyl group but is absent, if the nitrogen, to which $R^6$ is attached, carries a double-bond in the heterocyclic aromatic ring formed by Z, Z represents the atoms required to complete a substituted or unsubstituted, 5- or 6-membered, heterocyclic aromatic ring or a condensed system such as isoquinoline, which atomic group may contain other hetero atoms in addition to the nitrogen atom, e.g. oxygen or sulphur, and X represents an anion, e.g. halogen⁻, $BF_4^-$, $NO_3^-$, $SO_4^{31}$, $ClO_4^-$, or $CH_3OSO_3^-$.

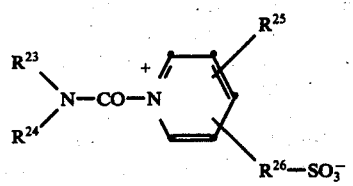

Me⁺X⁻ in which
- $R^{23}$, $R^{24}$ have the same meaning as $R^2$ and $R^3$,
- $R^{25}$ hydrogen, methyl, or ethyl,
- $R^{26}$ methylene, ethylene, propylene, or a single chemical bond,
- Me³⁰ an alkaline metal cation, e.g. Li³⁰, Na³⁰, K³⁰
- X³¹ an anion e.g. Cl⁻ and Br⁻.

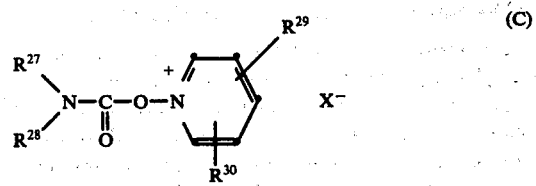

in which
- $R^{27}$ represents alkyl having 1 to 3 carbon atoms or aryl, e.g. phenyl,
- $R^{28}$ alkyl having 1 to 3 carbon atoms or the group

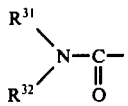

in which
- $R^{31}$ represents hydrogen or alkyl such as methyl or ethyl, and
- $R^{32}$ alkyl such as methyl or ethyl, or
- $R^{27}$ and $R^{28}$ together represent the atoms required to complete a heterocyclic ring system such as a pyrrolidine, morpholine, piperidine, perhydroazepine, 1,2,3,4-tetrahydroquinoline or imidazolidine-2-OH ring or
- $R^{27}$ and $R^{28}$ together represent the atoms required to complete a piperazine ring, which by its second nitrogen atom is linked to a similar second molecular group corresponding to the general formula,
- $R^{29}$ represents hydrogen, halogen e.g. chlorine and bromine, alkyl e.g. methyl and ethyl, oxyalkyl having 1 to 3 carbon atoms, cyano, —$CONH_2$ or —NH-CO-O alkyl (such as methyl and ethyl),
- $R^{30}$ represents hydrogen, alkyl e.g. methyl and ethyl, and
- X represents an anion such as $CL^-$, $BF_4^-$, or $ClO_4^-$ $$R^{31}-N=C=N-R^{32} \qquad (D)$$

in which
- $R^{31}$ and $R^{32}$ (similar or different) represent alkyl e.g. methyl, ethyl, n-propyl, isopropyl, n-butyl, s-butyl, isobutyl, t-butyl, amyl, hexyl, cyclohexyl, alkoxyalkyl e.g. methoxy or ethoxyethyl or -propyl, alkyl, aryl e.g. phenyl, benzyl, and β-phenylethyl, ethylmorpholinyl, diethylaminoethyl, ethylpyridyl, α- ,β-, and γ-methyl- or ethylpyridyl or
- $R^{31}$ represents alkyl having 1 to 5 carbon atoms and $R^{32}$ represents the group

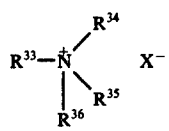

in which
- $R^{32}$ represents alkyl having 1 to 5 carbon atoms,
- $R^{34}$ and $R^{35}$ represent alkyl having 1 to 3 carbon atoms or
- $R^{34}$ and $R^{35}$ together form a 6-membered heterocyclic ring with one or two hetero atoms e.g. morpholine, piperidine, pyrrolidine,
- $R^{36}$ represents hydrogen or lower alkyl, and
- X represents an anion such as $Cl^-$, $Br^-$, or toluene sulphonate.

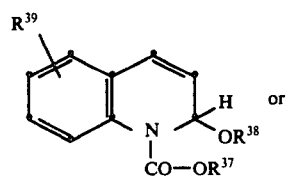

(E)

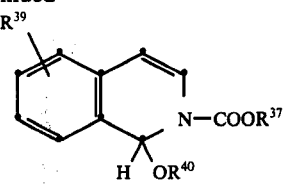

in which
- $R^{37}$ represents alkyl having 1 to 4 carbon atoms, which may be substituted with alkyloxy e.g. with methoxy or ethoxy, or with halogen e.g. with chlorine or bromine,
- $R^{38}$ alkyl having 1 to 4 carbon atoms, which may be substituted with alkoxy e.g. methoxy or ethoxy, with halogen e.g. chlorine, with dialkylamino or trialkylammonium, e.g. dimethyl or diethylamino, trimethyl or triethylammonium, with aryl e.g. phenyl, or with alkylsulphonyl e.g. methyl or ethylsulphonyl or $R^{38}$, if $R^{39}$ is absent, represents

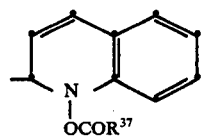

- $R^{39}$ hydrogen, halogen, e.g. chlorine or bromine, alkoxy e.g. methoxy or alkoxy, alkyl e.g. methyl, ethyl, or propyl,
- $R^{40}$ represents an alkyl group including a substituted alkyl group.

Details concerning the preparation and properties of these hardeners can be found in the above-mentioned publications. Preferred fast-acting hardeners for use in the colour photographic material according to the invention are the carbamoylpyridinium compounds of formulae A and B, and particularly the carbamoyloxypyridinium compounds of formula C.

The following are examples of fast-acting compounds according to formulae A to E: Compounds according to formula (A):

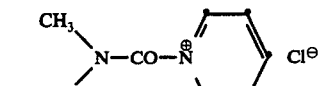

sirup, strongly hygroscopic

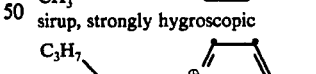

sirup, strongly hygroscopic

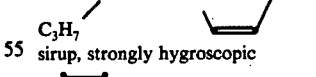

melting point 112° C

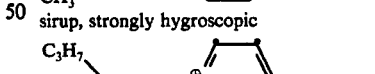

1.

2.

3.

4.

-continued
melting point 103° C
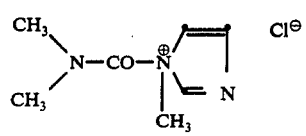
melting point 87–89° C
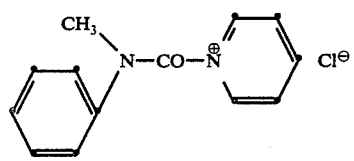
melting point 108–110° C
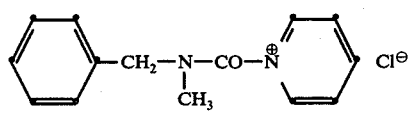
sirup, hygroscopic
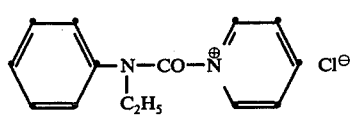
melting point 105–107° C
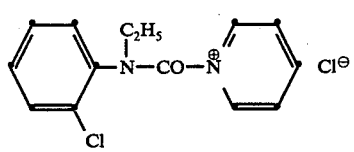
sirup
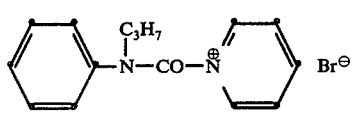
melting point 103–105° C
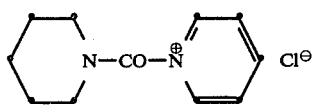
melting point 75–77° C
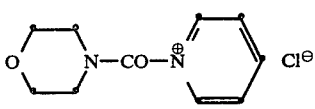
melting point 110–112° C
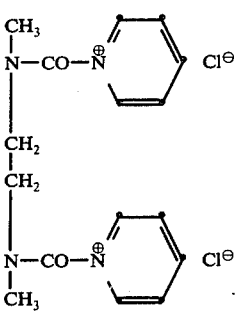
melting point 95–96° C
-continued
5. 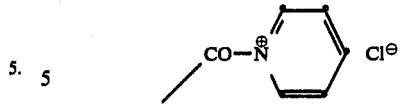
6. 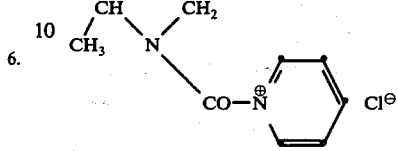
melting point 106° C
7. 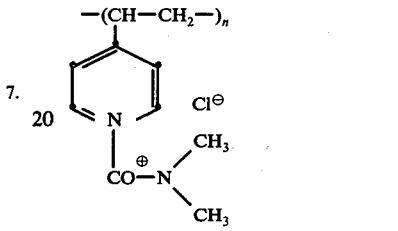
8. molecular weight higher than 10,000
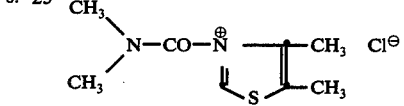
melting point 66–68° C
9. 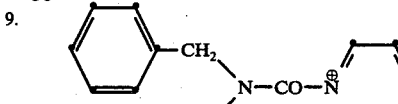
10. 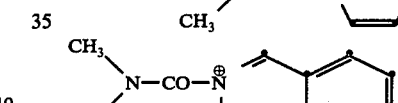
oil
11. 
melting point 103–105° C
12. 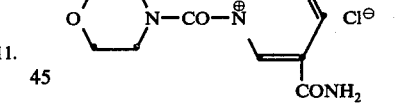
oil
13. 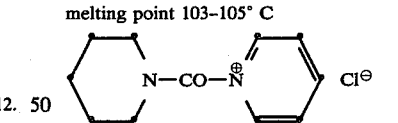
melting point 109° C
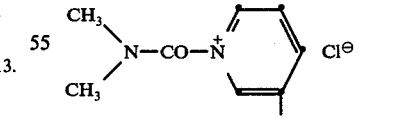
oil -continued
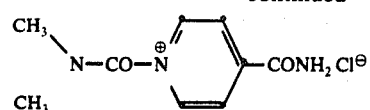
melting point 115° C
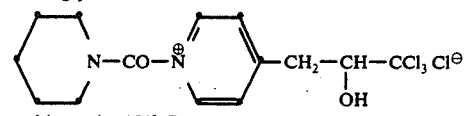
melting point 154° C
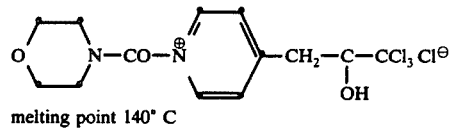
melting point 140° C
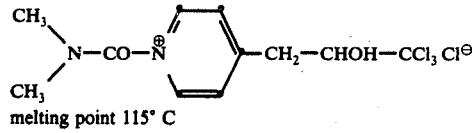
melting point 115° C
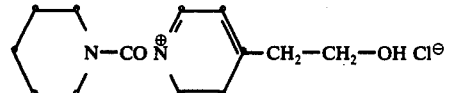
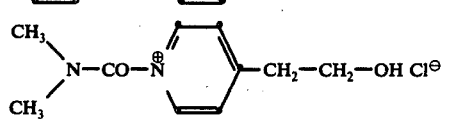
melting point 140–145° C
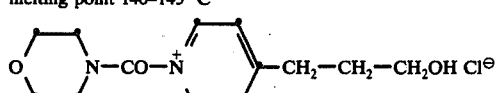
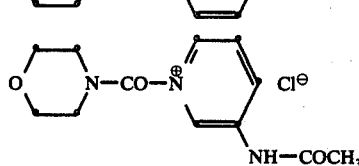
melting point 118–120° C
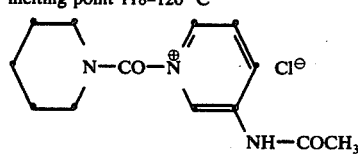
melting point 90° C
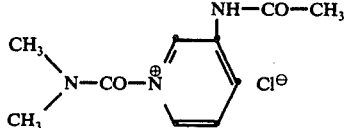
melting point 210° C
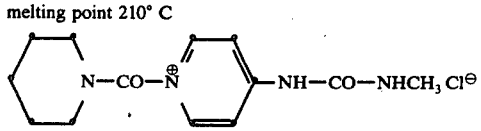
oil
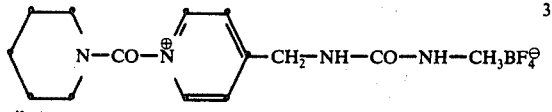
oil
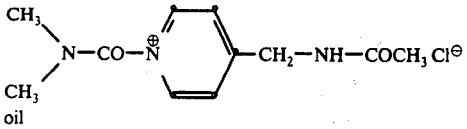
oil
24. 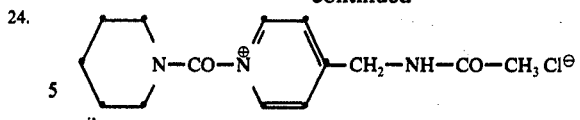
oil
25. 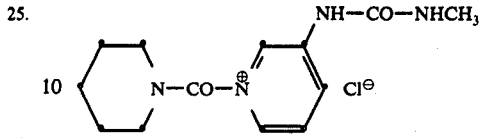
melting point: 60–65° C
26. 
27. 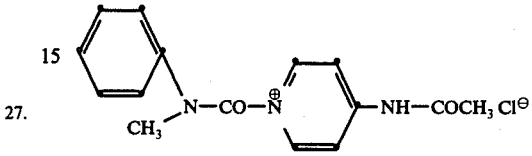
28. 
29. 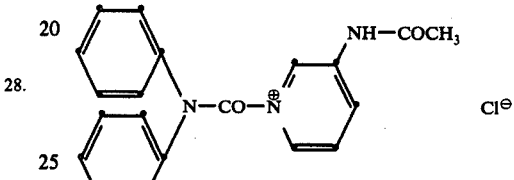
30. 
31. 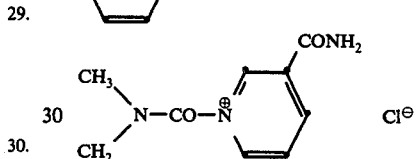
32. 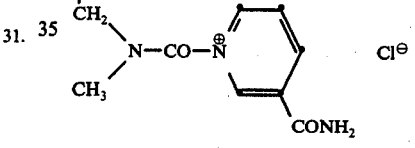
Compounds according to formula (B):
33. 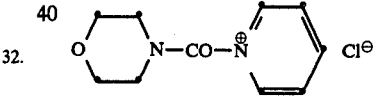
Na⊕ Cl⊖
34. 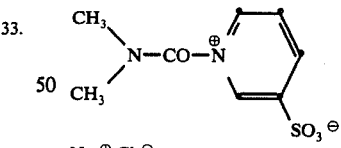
Na⊕ Cl⊖
35. 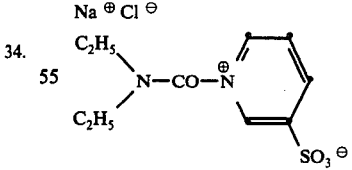
Na⊕ Cl⊖
36. 
37. 
38. 
39. 
40. 
41. 
42. 
1. 
2. 
3.

-continued
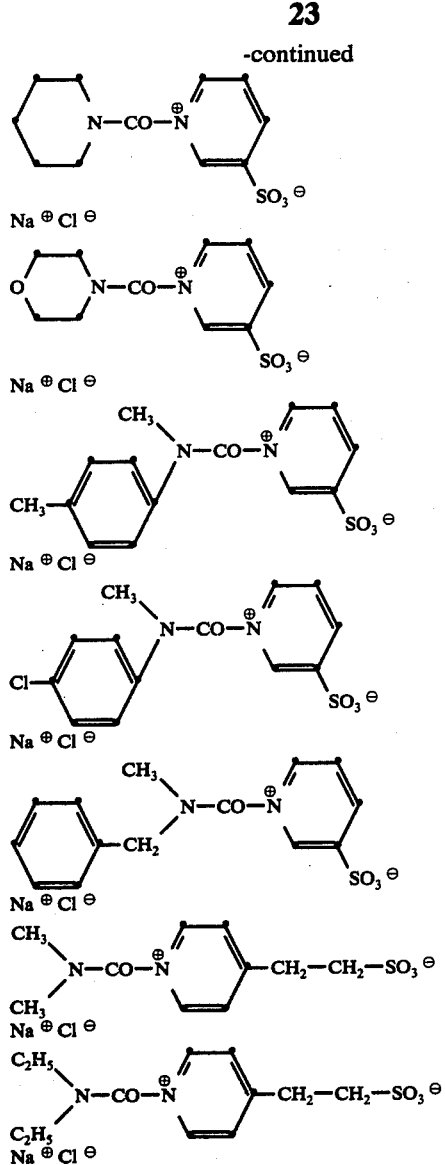
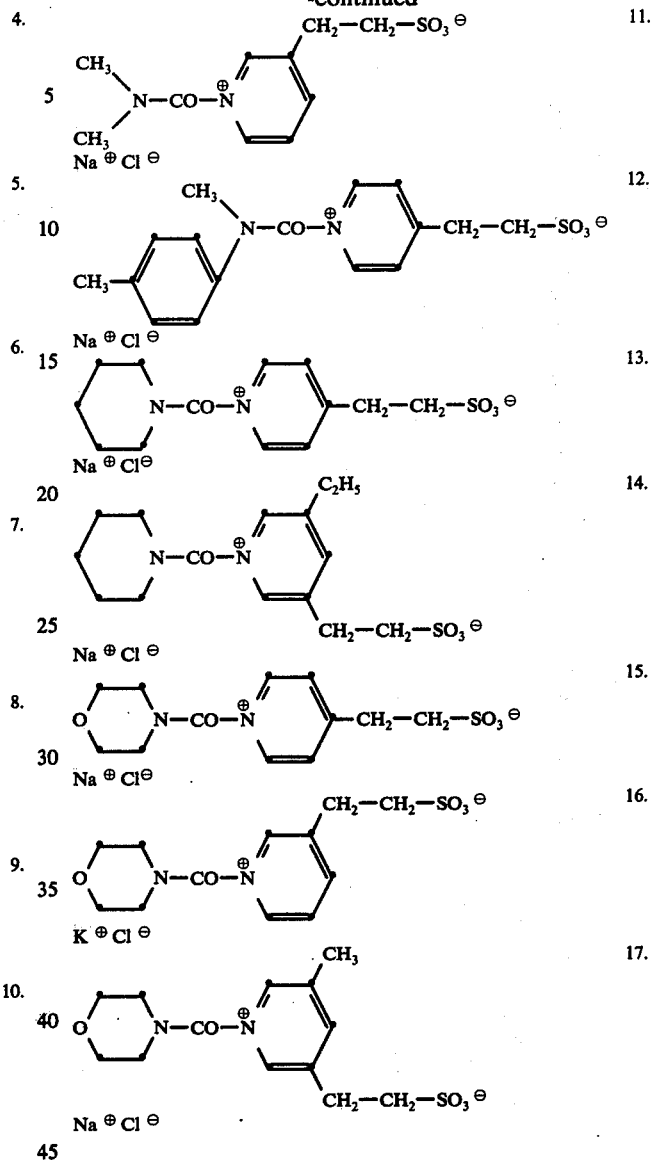
Compounds according to formula (C):
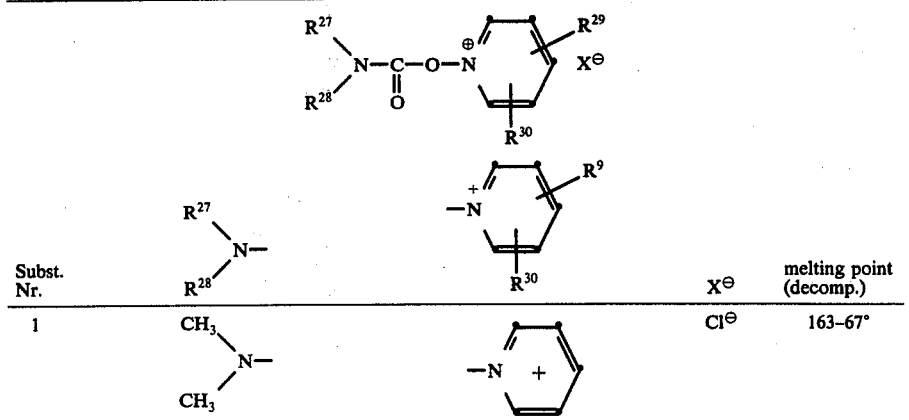
| Subst. Nr. | $R^{27}\!\!\diagdown\!\!N\!\!-\!\!/R^{28}$ | $R^{30}$, $R^9$ ring | $X^\ominus$ | melting point (decomp.) |
|---|---|---|---|---|
| 1 | $(CH_3)_2N-$ | pyridinium | $Cl^\ominus$ | 163–67° |

-continued

| Subst. Nr. | $\begin{matrix}R^{27}\\ \phantom{R}\diagdown N-\\ R^{28}\diagup\end{matrix}$ | (pyridinium group) | $X^\ominus$ | melting point (decomp.) |
|---|---|---|---|---|
| 2 | " | −N⁺ pyridinium with 4-CH₃ | Cl⊖ | 168–70° |
| 3 | " | −N⁺ pyridinium with CH₃ | Cl⊖ | 86° |
| 4 | " | −N⁺ pyridinium with C₂H₅ and CH₃ | Cl⊖ | 90° |
| 5 | " | −N⁺ pyridinium with Cl | ClO₄⊖ | 100–102° |
| 6 | " | −N⁺ pyridinium with OC₂H₅ | ClO₄⊖ | 95–100° |
| 7 | " | −N⁺ pyridinium with CH₃ | ClO₄⊖ | 100–102° |
| 8 | " | −N⁺ pyridinium with NH−C(O)−OC₂H₅ | ClO₄⊖ | 150° |
| 9 | $\begin{matrix}C_2H_5\\ \phantom{C}\diagdown N-\\ C_2H_5\diagup\end{matrix}$ | −N⁺ pyridinium | Cl⊖ | 108–110° |
| 10 | " | −N⁺ pyridinium with CH₃ | ClO₄⊖ | 64–65° |
| 11 | " | −N⁺ pyridinium with CH₃ | ClO₄⊖ | 130–32° |
| 12 | " | −N⁺ pyridinium with Cl | Cl⊖ | 95–100° |

-continued $$\begin{array}{c} R^{27} \\ \phantom{R^{27}}\diagdown \\ N-\underset{\underset{O}{\|}}{C}-O-\overset{\oplus}{N}\diagup\hspace{-2pt}\diagdown\hspace{-8pt}\begin{array}{c}R^{29}\\ \\ R^{30}\end{array} \quad X^{\ominus} \\ R^{28}\phantom{XXXX} \end{array}$$

| Subst. Nr. | $\begin{array}{c}R^{27}\\ \diagdown\\ N-\\ \diagup\\ R^{28}\end{array}$ | $-\overset{+}{N}\diagup\hspace{-2pt}\diagdown\hspace{-8pt}\begin{array}{c}R^{9}\\ \\ R^{30}\end{array}$ | $X^{\ominus}$ | melting point (decomp.) |
|---|---|---|---|---|
| 13 | pyrrolidino (CH₂CH₂–N–CH₂CH₂) | pyridinium | Cl$^{\ominus}$ | 114–115° |
| 14 | " | 4-CH₃-pyridinium | Cl$^{\ominus}$ | 132° |
| 15 | morpholino (O(CH₂CH₂)₂N–) | pyridinium | Cl$^{\ominus}$ | 132° |
| 16 | " | " | BF$_4^{\ominus}$ | 138–140° |
| 17 | " | " | ClO$_4^{\ominus}$ | 150–152° |
| 18 | " | 4-CH₃-pyridinium | Cl$^{\ominus}$ | 110–13° |
| 19 | " | " | ClO$_4^{\ominus}$ | 140–42° |
| 20 | " | 3-CH₃-pyridinium | Cl$^{\ominus}$ | 130–32° |
| 21 | " | " | ClO$_4^{\ominus}$ | 144–46° |
| 22 | morpholino | 4-CH₃-pyridinium | Cl$^{\ominus}$ | >90° |
| 23 | " | 4-C₂H₅-pyridinium | Cl$^{\ominus}$ | 100–102° |
| 24 | " | 2-CH₃-4-C₂H₅-pyridinium | Cl$^{\ominus}$ | 102–104° |
| 25 | " | 4-Cl-pyridinium | Cl$^{\ominus}$ | 100–102° |
| 26 | " | 4-OCH₃-pyridinium | Cl$^{\ominus}$ | 113–115° |
| 27 | " | 4-OC₂H₅-pyridinium | Cl$^{\ominus}$ | >115° |
| 28 | " | " | ClO$_4^{\ominus}$ | 112–14° |

-continued $$\underset{R^{28}}{\overset{R^{27}}{N}}-\underset{\underset{O}{\|}}{C}-O-\overset{\oplus}{N}\underset{R^{30}}{\overset{R^{29}}{\bigcirc}}\ X^{\ominus}$$

| Subst. Nr. | $\underset{R^{28}}{\overset{R^{27}}{N}}-$ | $-N\overset{+}{\underset{R^{30}}{\bigcirc}}R^9$ | $X^{\ominus}$ | melting point (decomp.) |
|---|---|---|---|---|
| 29 | " | pyridinium, 3-O-CH(CH$_3$)$_2$ | Cl$^{\ominus}$ | 93–95° |
| 30 | " | pyridinium, 2-OC$_2$H$_5$ | Cl$^{\ominus}$ | 65–70° |
| 31 | " | pyridinium, 3-OC$_2$H$_5$ | Cl$^{\ominus}$ | 65–70° |
| 32 | " | pyridinium, 2-CN | Cl$^{\ominus}$ | 80–82° |
| 33 | " | pyridinium, 4-NHCOCH$_3$ | ClO$_4^{\ominus}$ | 150° |
| 34 | " | pyridinium, 3-NH—CO—OC$_2$H$_5$ | ClO$_4^{\ominus}$ | 162–63° |
| 35 | " | pyridinium, 2-CONH$_2$ | ClO$_4^{\ominus}$ | 200° |
| 36 | $\underset{CH_3-CH}{\overset{CH_3-CH}{\underset{CH_3}{\overset{CH_3}{}}}}\!\!\!N-$ | pyridinium | Cl$^{\ominus}$ | 158° |
| 37 | " | pyridinium, 2-CH$_3$ | Cl$^{\ominus}$ | 138° |
| 38 | " | pyridinium, 3-CH$_3$ | Cl$^{\ominus}$ | 152–154° |

-continued $$\begin{array}{c}R^{27}\\ \diagdown\\ N-C-O-N^{\oplus}\\ \diagup\quad\parallel\\ R^{28}\quad O\end{array}\begin{array}{c}R^{29}\\ \\ R^{30}\end{array}X^{\ominus}$$

| Subst. Nr. | $\begin{array}{c}R^{27}\\ \diagdown\\ N-\\ \diagup\\ R^{28}\end{array}$ | $\begin{array}{c}\\ -N^{+}\\ \\ R^{30}\end{array}\begin{array}{c}R^{9}\\ \end{array}$ | $X^{\ominus}$ | melting point (decomp.) |
|---|---|---|---|---|
| 39 | piperidinyl (CH₂-CH₂-CH₂-CH₂-N-) | pyridinium | $Cl^{\ominus}$ | 85–86° |
| 40 | " | 2-CH₃-pyridinium | $ClO_4^{\ominus}$ | 100° |
| 41 | " | 3-CH₃-pyridinium | $ClO_4^{\ominus}$ | 80° |
| 42 | " | 4-Cl-pyridinium | $Cl^{\ominus}$ | 104–106° |
| 43 | hexamethyleneimino (CH₂-CH₂-CH₂-CH₂-CH₂-CH₂-N-) | pyridinium | $Cl^{\ominus}$ | 76–78° |
| 44 | indolinyl (C₆H₄-CH₂-CH₂-N-) | " | $Cl^{\ominus}$ | 140–144° |
| 45 | diphenylamino ((C₆H₅)₂N-) | pyridinium | $Cl^{\ominus}$ | 160–162° |
| 46 | " | 3-CH₃-pyridinium | $Cl^{\ominus}$ | 98–100° |
| 47 | " | 4-CH₃-pyridinium | $Cl^{\ominus}$ | 218–220° |
| 48 | " | 2-CH₃-pyridinium | $Cl^{\ominus}$ | 116° |
| 49 | " | 4-Cl-pyridinium | $Cl^{\ominus}$ | 125–128° |

-continued

| Subst. Nr. | $\begin{matrix} R^{27} \\ N- \\ R^{28} \end{matrix}$ | pyridinium ring with $R^9$, $R^{30}$ | $X^\ominus$ | melting point (decomp.) |
|---|---|---|---|---|
| 50 | 2,6-dimethylpiperazine-1,4-diyl | 2x—N⁺-pyridinium | Cl⁻ | 109–112° |
| 51 | CH₃—NH—C(O)—N(CH₃)₂ | —N⁺-pyridinium | Cl⁻ | 87–89° |
| 52 | " | —N⁺-pyridinium (4-CH₃) | Cl⁻ | 105° |
| 53 | " | —N⁺-pyridinium (3-CH₃) | Cl⁻ | 88–89° |
| 54 | (CH₃)₂N—C(O)—N(CH₃)(CH₂CH₃) | —N⁺-pyridinium | Cl⁻ | 168–170° |
| 55 | (CH₃)₂N—C(O)—N(CH₃)((CH₂)₂CH₃) | " | Cl⁻ | 169–173° |
| 56 | (C₂H₅)₂N—C(O)—N(CH₃)((CH₂)₂CH₃) | " | Cl⁻ | 173–180° |
| 57 | (C₂H₅)₂N—C(O)—N(CH₃)(C₂H₅) | " | Cl⁻ | 173–183° |
| 58 | imidazolidin-2-one-1,3-diyl (HN—CH₂—CH₂—N—C(O)) | " | Cl⁻ | 221–223° |
| 59 | " | —N⁺-pyridinium (3-CH₃) | Cl⁻ | 180–185° |

Compounds according to formula (D):

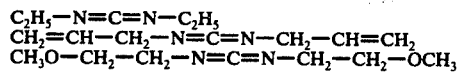

1. $C_2H_5-N=C=N-C_2H_5$
2. $CH_2=CH-CH_2-N=C=N-CH_2-CH=CH_2$
3. $CH_3O-CH_2-CH_2-N=C=N-CH_2-CH_2-OCH_3$

-continued

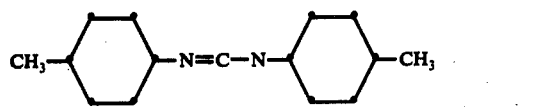  4.

$C_2H_5-(CH_3)CH-N=C=N-CH(CH_3)-C_2H_5$  5.
$(C_2H_5)_2N-CH_2-CH_2-N=C=N-CH_2-CH_2-N(C_2H_5)_2$  6.
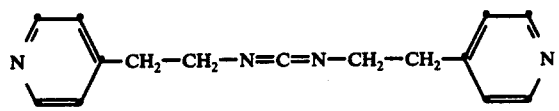  7.

$CH_3-N=C=N-CH(CH_3)_2$  8.
$C_2H_5-N=C=N-(CH_2)_2-OCH_3$  9.
  10.
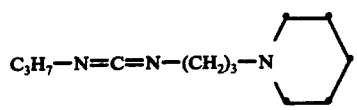

11.
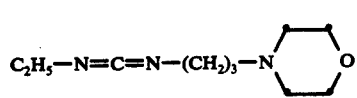

12.
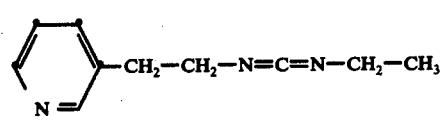

13.
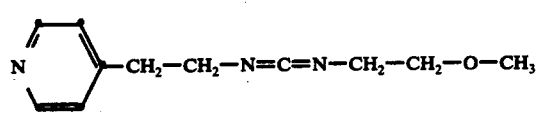

14.
$CH_3-N=C=N-(CH_2)_3-\overset{\oplus}{\underset{H}{N}}(CH_3)_2$   Cl$^\ominus$ 15.
$C_2H_5-N=C=N-(CH_2)_3-\overset{\oplus}{\underset{H}{N}}(CH_3)_2$   Cl$^\ominus$ 16.
$C_2H_5-N=C=N-(CH_2)_3-\overset{\oplus}{N}(CH_3)_3$   Cl$^\ominus$ 17.
$C_5H_{11}-N=C=N-(CH_2)_3-\overset{\oplus}{\underset{H}{N}}(C_2H_5)_2$   Cl$^\ominus$ 18.
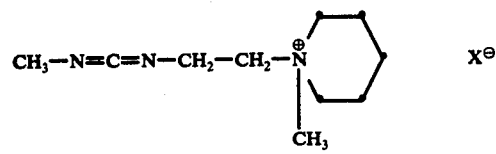   X$^\ominus$ 19.
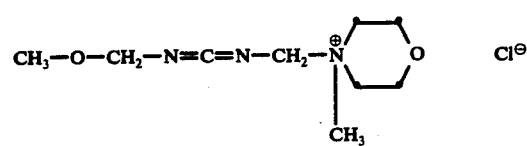   Cl$^\ominus$ 20.
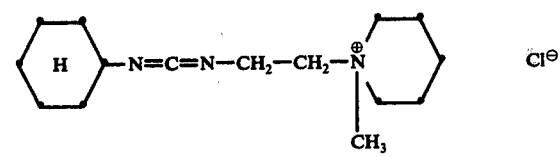   Cl$^\ominus$ 21.
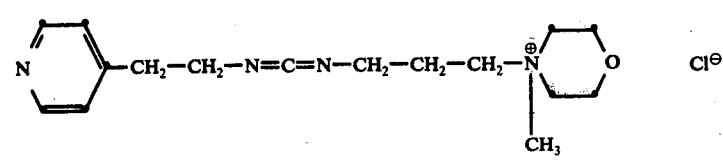   Cl$^\ominus$ Compounds according to formula (E)

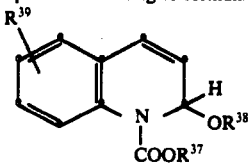

| Nr. | R³⁷ | R³⁸ | R³⁹ | Boiling point (° C) | Melting point (° C) |
|---|---|---|---|---|---|
| 1 | CH₃ | CH₃ | H | 130° (0,3) | |
| 2 | C₂H₅ | C₂H₅ | H | | 64–66° |
| 3 | CH₃ | C₂H₅ | H | | 75–76° |
| 4 | C₂H₅ | CH₃ | H | 135–140° (0,6) | |
| 5 | CH₃ | (CH₂)₂ . CH₃ | H | 135–140° (0,3) | |
| 6 | CH₃ | CH . (CH₃)₂ | H | 180–185° (0,4) | |
| 7 | CH₃ | (CH₂)₂ . OCH₃ | H | 180–168° (0,6) | |
| 9 | CH₃ | (CH₂)₂ . SO₂ . CH₃ | H | non-distillable oil | |
| 10 | CH₃ | (CH₂)₂ . SO₂ . C₂H₅ | H | non-distillable oil | |
| 11 | CH₃ | (CH₂)₂ . Cl | H | 135–150° (0,5) | |
| 12 | CH₃ | (CH₂)₂ . N⁺(CH₃)₃ Cl⁻ | H | | |
| 13 | C₂H₅ | (CH₂)₂ . CH₃ | H | 140–145° (1,0) | |
| 14 | C₂H₅ | CH . (CH₃)₂ | H | 130–134° (0,5) | |
| 15 | C₂H₅ | (CH₂)₂ . OCH₃ | H | 160–165° (0,25) | |
| 16 | C₂H₅ | (CH₂)₂ . OC₂H₅ | H | 175–180° (0,25) | |
| 17 | C₂H₅ | CH₂ . C₆H₅ | H | 180–185° (0,15) | |
| 18 | C₂H₅ | (CH₂)₂ . C₆H₅ | H | 180–190° (0,15) | |
| 19 | C₂H₅ | (CH₂)₂ . SO₂ . CH₂ . CH₃ | H | non-distillable oil | |
| 20 | C₂H₅ | (CH₂)₂ . Cl | H | 135–145° (0,5) | |
| 21 | C₂H₅ | (CH₂)₂ . N⁺(CH₃)₃Cl⁻ | H | | 140° (decomp.) |
| 22 | C₂H₅ | (CH₂)₃ . CH₃ | H | 137–139° (0,5) | |
| 23 | (CH₂)₂ . OCH₃ | CH₃ | H | 175–180° (0,3) | |
| 24 | (CH₂)₂ . OCH₃ | (CH₂)₂ . OCH₃ | H | 180–185° (0,3) | |
| 25 | C₂H₅ | C₂H₅ | (5) SO₃Na | sirup | |
| 26 | C₂H₅ | C₂H₅ | (8) OCH₃ | 160 (0,5) | |

The fast-acting hardeners can be added in aqueous or alcoholic solution to the protein layers to be hardened, especially to gelatin layers, prior to the coating thereof.

The hardeners have to be added immediately before the coating since they enter into reaction very quickly with gelatin or the other proteins commonly used in photography. After the hardeners had been added, the coating solutions have to be coated within a few minutes. The speed, at which the hardening reaction takes place, depends mainly upon the concentrations of the proteins in the coating solution.

The concentrations, at which the hardeners according to the invention are used in the coating solution may vary within wide limits and depend mainly upon the particular compound used as hardener.

Satisfactory results are obtained with quantities of 0.1 to 10% by weight and preferably 0.2 to 5% by weight based on the dry weight of binder.

It is also possible to coat non-hardening coating solutions first and then to cover the thus obtained layers with a solution of the hardening compounds. It is advantageous to use in this solution a high molecular compound as film forming colloid, which does not enter into reaction with the hardener and has good film forming properties. Polysaccharides described in the published German Patent Application No. 2,417,779 have proved to be very appropriate for this purpose. Suitable polysaccharides are straight-chain polymers, in which either (A) at least one third of the monosaccharide units are linked in the 1-2-position and the remaining monosaccharide units are linked in the 1-4-position, or (B) substantially all the monosaccharide units are linked in the 1-4-position and at least 50% of the hydroxyl groups of the monosaccharide units are acetylated or replaced by an OSO₃Me group in which Me represents an alkali metal.

Examples of such polysaccharides include the polymers, which can be synthetized by biosynthesis from special strains of bacteria and which are named after the bacteria that bring about this biosynthesis, e.g. B-1459 and B-1973. This nomenclature is conventionally used in literature and makes it possible for the polysaccharides to be identified unequivocally. Further information on the two above-mentioned polysaccharides B-1459 and B-1973 can be found in the papers by D. C. Orentaset al, Can.J.Microbiol., 9, 427 (1963); J. H. Sloneker et al, Can. J. Chem., 46, 3, 353 (1968); L. L. Wallen at al, Appl.Microbiol., 13, 272 (1965); M. E. Slodke, Biochem.Biophys. Acta 69; and in the U.S. Pat. Nos. 3,000,790 — 3,383,307 — 3,391,061 and 3,516,983.

A further example of a ploysacharise suitable for the proces of the invention is the cellulose sulphate KELCO SCS, supplied by KELCO Company, New Jersey, USA, to which the following formula is attributed:

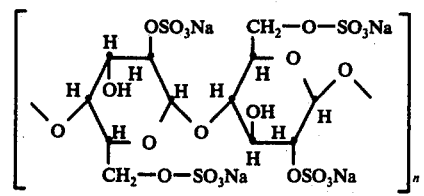

Another trade product of KELCO Company suitable for the process of the invention is KELZAN, which corresponds to the polysaccharide B-1459.

The quantitites of polysaccharide and hardener to be employed depend mainly upon the nature of the material to be hardened, the number and the thickness of the layers to be hardened, the quantity of composition to be applied, and the polysaccharide used. The commercial polysaccharides, e.g. those supplied by Kelco and graded HV (High-Viscosity), MV (Medium-Viscosity), and LV (Low-Viscosity) allow for wide variations in the quantity applied wet or in the resulting thickness of the layer. Satisfactory results are generally obtained with coating solutions containing 1 to 20 g of polysaccharide and 5 to 50 g of hardener per 1000 ml of water applied in a quantity corresponding to 20 to 100 g/sq.m when wet if the solutions are required for hardening a photographic three-colour-negative material of conventional structure. A photographic material treated in this way will in any case be capable of withstanding the mechanical stress produced by machine processing at 30 to 40° C after it has been dried and stored for one day. Without regard to the structure of the phototgraphic material it can be said that 0.1 to 10% by weight of hardener according to the invention, based on the dry weight of the binder to be hardened, suffices to produce a photographic material that can be processed at 30 to 40° C.

It is also possible to introduce the hardeners in a form of aqueous solutions during the procesing of the photographic material e.g. prior to the development, into the non-hardened or slightly hardened photographic layers.

The fast-acting hardeners can be used either alone or combined. Furthermore the compounds can be combined with any compounds from the classes of hardeners previously known, e.g. formaldehyde, mucochloric acid, triacrylformal, bisvinylsulphones bisvinylsulphonamides, dialdehydes, or bischloroacetamides, or inorganic salts, e.g. chormium (III), aluminium (III), and zirconium salts.

The colloid layers to be hardened of the colour material according to the invention may contain in addition to gelatin water-soluble high polymeric compounds, in particular polyvinyl acohol, the sodium salt of polyacrylic acid, and other copolymers containing carboxyl groups, polyvinyl pyrrolidone, polyacrylamide or high molecular weight natural substances such as dextranes, dextrines, starch ether, alginic acid, or derivatives of alginic acid.

The 2-pyrazolin-5-on coupler precursors according to formulae I and II having a ballasting group in the 1- or 3-position can be incorporated into the photographic silver halide material according to any suitable known process. The couplers are incorporated preferably into photographic hydrophilic colliod media from solutions in high boiling sparingly water-miscible solvents such as di-n-butyl phthalate and tricresyl phosphate or in low boiling sparingly water-miscible solvents such as ethyl acetate, methylene chloride, diethyl carbonate, chloroform, and the like, or mixtures thereof.

For this purpose these solutions can be dispersed in extremely fine droplets, preferably in the presence of one or more wetting or dispersing agents, into the hydrophilic colloid medium e.g. aqueous gelatin, or into water, the low boiling sparingly water-miscible solvent being removed then by evaporation. The stable dispersions of the colour couplers can be stored as such and then admixed whenever desired with the very coating composition of the hydrophilic colloid layer such as a silver halide emulsion layer, into which the coupler precursors have to be preent.

Of course, the coupler precursors can be incorporated in another way into the hydrophilic colloid medium.

More details about particularly suitable techniques that may be employed for incorporating the coupler precursors into a hydrophilic colloid layer of a photographic material can be found in the U.S. Pat. Nos. 2,269,158 — 2,284,887 — 2,304,939 — 2,304,940, and 2,322,027, the United Kingdon patent specifications Nos. 791,219 — 1,098,594 — 1,099,414 — 1,099,415 — 1,099,416 — 1,099,417 — 1,218,190 — 1,272,561 — 1,297,347 and 1,297,947, the French Patent Specification No. 1,555,663, the Belgian Patent Specification No. 722,026, and the German Patent Specification No. 1,127,714.

The coupler precursors and fast-acting hardeners can be used in conjunction with various kinds of photographic emulsions. Various silver salts can be used as sensitive salt e.g. silver bromide, silver iodide, silver chloride, or mixed silver halides such as silver chlorobromide, silver bromoiodide, and silver chlorobromoiodide. The coupler precursors can be used in emulsions of the mixed packet type as described in the U.S. Pat. No. 2,698,794 or emulsions of the mixed grain type as described in the U.S. Pat. No. 2,592,243. The coupler precursors can be used with emulsions in which latent images are formed predominantly at the surface of the silver halide crystals, or with emulsions in which latent images are formed predominantly inside the silver halide crystals.

The hydrophilic colloid used as the vehicle for the silver halide may be e.g. gelatin, colloid albumin, zein, casein, a cellulose derivative, a synthetic hydrophilic colloid such as polyvinyl alcohol, poly-N-vinylpyrrolidone, etc. If desired, compatible mixtures of 2 or more of these colloids can be employed for dispersing the silver halide.

The light-sensitive silver halide emulsions for use in the preparation of a photographic material according to the present invention can be sensitized chemically as well as optically. They can be sensitized chemically by effecting the ripening in the presence of small amounts of sulphur-containing compounds such as allyl thiocyanate, allyl thiourea, sodium thiosulphate, etc. The emulsions can also be sensitized by means of reductors, e.g. tin compounds as described in the French Patent Specification No. 1,146,955 and in the Belgian Patent Specification No. 568,687, imino-aminomethanesulphinic acid compounds as described in the United Kingdom patent specification No. 789,823 and small amounts of noble metal compounds such as gold, platinum, palladium, iridium, ruthenium, and rhodium compounds. They can be sensitized optically by means of cyanine and merocyanine dyes.

The emulsions can also comprise compounds that sensitize by development acceleration e.g. compounds of the polyoxyalkylene type such as alkylene oxide condensation products as described i.e. in the U.S. Pat. Nos. 2,531,832 — 2,533,990 — 3,158,484, and 3,210,191, in the United Kingdom Patent Specifications Nos. 920,637 and 991,608, and in the Belgian Patent Specification No. 648,710, and onium derivatives of amine oxides, as described in the United Kingdom patent specification No. 1,121,696.

The emulsions may comprise stabilizers e.g. heterocyclic nitrogen-containing thioxo compounds such as benzothiazoline 2-thione and 1-phenyl-2-tetrazolin-5-thione and compounds of the hydroxytriazolopyrimidine type. They can also be stabilized with mercury compounds such as the mercury compounds described in the Belgian Patent Specification Nos. 524,121 — 677,377, and 707,386, and in the U.S. Pat. No. 3,179,520.

The light-sensitive emulsions may comprise any other type of ingredients such as plasticizers, hardeners, wetting agents, etc.

The non-diffusing magenta coupler precursors described in the present invention are incorporated usually into the green-sensitized silver halide emulsion for forming one of the differently sensitized silver halide emulsion layers of a photographic multilayer colour material. Such photographic multilayer colour material usually comprises a support, a red-sensitized silver halide emulsion layer with a cyan colour coupler, a green-sensitized silver halide emulsion layer with a magenta colour coupler, and a blue-sensitive silver halide emulsion layer with a yellow colour coupler.

The emulsions can be coated on a wide variety of photographic emulsion supports. Typical supports include cellulose ester film, polyvinylacetal film, polystyrene film, polyethyleneterephthalate film, and related films or resinous materials, as well as paper and glass. It is also possible to employ paper coated with $\alpha$-olefin polymers e.g. paper coated with polyethylene, polypropylene, ethylene butylene copolymers, etc.

The colour photographic materials according to the invention can be developed with any of the known aromatic primary amino colour developing substances e.g. p-phenylenediamine and derivatives thereof such as N,N-diethyl-p-phenylenediamine, N-butyl-N-sulphobutyl-p-phenylenediamine, 2-amino-5-diethyl-aminotoluene, 4-amino-N-ethyl-N($\beta$-methanesulphonamidoethyl)-m-toluidine, N-hydroxyethyl-N-ethyl-p-phenylenediamine, 4-amino-3-methyl-N-ethyl-N-($\beta$-hydroxyethyl)aniline, etc.

It may be advisable to accelerate the setting free of the 2-pyrazolin-5-one coupler from the coupler precursor during the development. For this purpose organic amines can be added to the developer or the material to be developed can be treated before the development with an alkaline solution containing an organic amine, as described in the U.S. Defensive Publication No. T 887007.

Suitable organic amines are primary, secondary, and tertiary amines as well as saturated and unsaturated cyclic amines. Representative examples of amines are alkyl-, dialkyl-, and trialkylamines, in which the alkyl group may be substituted and have an aliphatic chain of 1 to 10 carbon atoms, preferably of 1 to 4 carbon atoms, e.g. methyl, ethyl, propyl, isopropyl, butyl, isobutyl, s-butyl and t-butyl, etc., e.g. methylamine, ethylamine, allylamine, trimethylamine, triethylamine, 2-aminoethanol, etc.; arylamine such as aniline, dimethylaniline, etc.; alkyldiamines, the alkyl group of which may be substituted and have an aliphatic chain of 2 to 10 carbon atoms, preferably of 2 to 4 carbon atoms, e.g. ethyl, propyl, butyl etc., such as ethylenediamine, propylenediamine etc.; unsaturated cyclic amines e.g. pyridine, imidazole etc.; saturated cyclic amines, wherein the amine-nitrogen atom is a part of a 4- to 6-membered ring, e.g. piperidine, indoline, 1,4-ethylenepiperidine etc.; azines including alkyl- and arylazines, wherein the alkyl group contains 1 to 4 carbon atoms, e.g. methyl, ethyl, propyl, butyl etc., such as hydrazine, 1,1-dimethylhydrazine, phenylhydrazine, nitrophenylhydrazine, dinitrophenylhydrazine, etc.

The following examples illustrate the invention.

EXAMPLE 1

117 g of silver bromoiodide emulsion (2-3 mole % of iodide) containing per kg an amount of silver halide equivalent to 47 g of silver nitrate as well as 73.4 g of gelatin were diluted with 192.5 g of a 7.5% aqueous gelatin solution and 200 g of distilled water. The resulting emulsion was admixed with an emulgate obtained by dissolving 0.006 mole of colour coupler 22 in 18 ml of ethyl acetate, dispersing the solution in 100 ml of a 5% aqueous gelatin solution in the presence of a dispersing agent by means of an ultrasonic wave generator, and eliminating the ethyl acetate by evaporation under reduced pressure. After neutralization of the emulsion and addition of the usual ingredients distilled water was added to make 720 g.

In the same way an emulsion was prepared, which instead of the acylated colour coupler contained the non-acylated one.

The emulsions obtained were coated on a cellulose triacetate support in a ratio of 125 g per m2 and then covered with an aqueous gelatin solution of hardener C 15 in an amount of 2.6% by weight based on the dry weight of gelatin of the emulsion layer.

The dried materials were exposed for 1/20 s through a continuous wedge having a constant of 0.3 and developed subsequently for 10 minutes at 22° C in a developing bath having the following composition:

| | |
|---|---|
| 2-amino-5-diethylaminotoluenehydrochloride | 3 g |
| sodium hexametaphosphate | 2 g |
| anhydrous sodium sulphite | 4 g |
| anhydrous sodium carbonate | 17 g |
| potassium bromide | 2 g |
| water to make | 1 liter |

The developed materials were treated for 5 minutes at 24° C in an intermediate bath containing 200 g of sodium thiosulphate per litre of water, rinsed for 10 min in water, and treated in a potassium bichromate bleaching bath.

The bleached materials were rinsed for 5 min in water and fixed in an aqueous solution of 200 g of sodium thiosulphate per liter.

After a final rinsing in water of 10 min the materials were dried. Magenta wedges having the following photographic cgaracteristics were obtained:

| Colour coupler | Relative sensitivity | Gamma | $D_{max}$ |
|---|---|---|---|
| non-acylated | 100 | 1.20 | 1.85 |
| acylated | 98 | 1.21 | 2.07 |

EXAMPLE 2

Example 1 was repeated with the difference that instead of the acylated coupler 22 the acylated coupler 9 was used.

The materials were exposed for 1/20 s to a continuous wedge having a constant of 0.3 and developed subsequently for 8 min and 20° C in a developing bath having the following composition:

| | |
|---|---|
| N,N-diethyl-p-phenylenediamine sulphate | 2.75 g |
| hydroxylaminesulphate | 1.2 g |
| sodium hexametaphosphate | 4 g |
| anhydrous sodiumsulphite | 2 g |
| anhydrous potassium carbonate | 75 g |
| potassium bromide | 2.5 g |
| water to make | 1 liter |

The developed materials were treated for 2 min at 18°-20° C in an intermediate bath containing 30 g of sodium thiosulphate in 1 liter of water.

The materials were rinsed for 15 min and then treated in a bleaching bath having the following position:

| | |
|---|---|
| borax | 20 g |
| anhydrous potassium bromide | 15 g |
| anhydrous sodium hydrogensulphite | 4.2 g |
| potassium cyanoferrate(III) | 100 g |
| water to make | 1 liter |

The bleached materials were rinsed for 5 min and fixed in an aqueous solution of 200 g of sodium thiosulphate per liter.

After a final rinsing in water of 15 min the materials were dried.

Magenta wedges and the following photographic characteristics were obtained:

| Colour coupler | Relative sensitivity | Gamma | $D_{max}$ |
|---|---|---|---|
| non-acylated | 100 | 0.60 | 1.04 |
| acylated | 100 | 0.88 | 2.22 |

When the emulsion layers had not been coated with a solution of hardener C 15, but with a conventional gelatin anti-stress layer, a maximum density of 2.20 was obtained for the material containing the non-acylated colour coupler and of 2.46 for the material containing the acylated colour coupler.

EXAMPLE 3

Example 2 was repeated with the difference that the materials now contain the acylated coupler 3 and the corresponding non-acylated coupler.

Magenta wedges having the following photographic characteristics were obtained:

| Colour coupler | Relative sensitivity | Gamma | $D_{max}$ |
|---|---|---|---|
| non-acylated | 100 | 1.00 | 1.66 |
| acylated | 98 | 0.85 | 2.00 |

EXAMPLE 4

Strips of a photographic material consisting of a film support and two green-sensitized silverbromoiodide emulsion layers coated with a gelatin antistress layer contain 14 g of gelatin and an amount of silver halide equivalent to 1.4 g of silver nitrate, and 1.3 mmole of colour coupler per sq.m. The colour couplers were incorporated into the emulsion from a solution in ethyl acetate and tricresyl phosphate, whereupon the ethyl acetate was removed by evaporation.

The gelatin antistress layers were coated with an aqueous solution of hardener C 15 in an amount of 7% by weight calculated on the dry weight of gelatin of the strips.

The strips were then exposed to a continuous wedge, developed for 4 min 30 s at 25° C in a common developing bath containing N,N-diethyl-p-phenylenediamine sulphate, and further treated in the usual way in a bleaching bath and a fixing bath.

In the following table the maximum density values ($D_{max}$) of the magenta wedges obtained as well as the scratch resistance values of the strips of photographic material are given. The values of scratch resistance constitute the weight (in gram) applied to a steel ball having a diameter of 6.4 mm, required to make this ball penetrate into the wet photographic layers down to the very support, when the ball is passed over the material.

Table

| Strip | Magenta coupler | $D_{max}$ | Scratch resistance |
|---|---|---|---|
| 1 | 1 | 1.66 | 1300 |
| 2 | 3 | 1.66 | 1300 |
| 3 | non-acylated form of coupler 1 and 3 | 1.35 | 700 |

EXAMPLE 5

Strips were made as described in example 4 with the difference that hardener A 30 was used now.

The strips were exposed to a continuous wedge, developed for 4 min 30 s at 25° C in a common colour developing bath containing 4-amino-3-methyl-N-ethyl-N-($\beta$-hydroxyethyl)anilinesulphate, and treated in the usual way in a bleaching bath and a fixing bath.

In the following table the maximum density values ($D_{max}$) of the magenta wedges obtained as well as the values of the scratch resistance as defined in example 4 are given.

Table

| Strip | Magenta coupler | Scratch resistance | $D_{max}$ |
|---|---|---|---|
| 1 | 1 | 1450 | 1.65 |
| 2 | 3 | 1450 | 1.44 |
| 3 | non-acylated form of coupler 1 and 3 | 800 | 1.08 |

EXAMPLE 6

Example 5 is repeated with the difference that hardener B 5 was used and that the treatment of the exposed strips occurred at increased temperature (38° C, developing time: 3 min).

Table

| Strip | Colour coupler | $D_{max}$ | Scratch resistance |
|---|---|---|---|
| 1 | 1 | 2.23 | 1200 |
| 2 | 3 | 1.96 | 1400 |
| 3 | non-acylated form of coupler 1 and 3 | 1.78 | 1400 |

EXAMPLE 7

Strips of material as described in example 1 and containing couplers 3, 9, 16, and 30 were prepared. The strips were developed as described in example 2 and the colour strips obtained in this way were exposed in a xenon illuminating device for $2.4 \times 10^6$ lux-hours and to a projection screen for $4.10^6$ lux-hours. For comparison analogous strips were prepared, exposed, developed, and irradiated, which strips instead of the acylated couplers 3, 9, 16, and 30 contained corresponding non-acylated couplers.

The decrease in colour densities of the irradiated samples, as compared with non-irradiated samples, measured at density 1.05 is given in % of the following table. The colour density at D = 1.05 decreases far less in the case of acylated couplers than in the case of non-acylated couplers. Indeed, the acylated component brings about the stabilization of the dye.

| Coupler | xenon test | projection screen |
|---|---|---|
| 3 (acylated) | 18 | 28 |
| non-acylated | 28 | 42 |
| 9 (acylated) | 12 | 8 |
| non-acylated | 35 | 30 |

-continued

| Coupler | xenon test | projection screen |
|---|---|---|
| 16 (acylated) | 8 | 4 |
| non-acylated | not determined | 17 |
| 30 (acylated) | 8 | 14 |
| non-acylated | 24 | 32 |

EXAMPLE 8

Emulsions were prepared as described in example 1 containing one of the colour coupler precursors 25, 26 and the parent non-acylated coupler.

All emulsions were coated on a cellulose triacetate support in a ratio of 125 g per sq.m and then covered with an aqueous gelatin solution of hardener $C_{15}$ in an amount of 5 % by weight based on the dry weight of gelatin of the emulsion layer.

The materials were exposed and processed as described in example 1.

Magenta wedges with the max.density values listed in the table were obtained.

| Coupler | $D_{max}$ |
|---|---|
| 25 | 2.53 |
| 26 | 2.81 |
| non-acylated | 1.26 |

When the emulsion with non-acylated coupler was not used with a fast-acting hardener but with a conventional antistress layer max.density was 2.65.

We claim:

1. Colour photographic silver halide material containing a fast-acting hardener selected from the group consisting of carbodiimides, dihydroquinolines, carbamoyl pyridiniums and carbamoyloxy pyridiniums wherein said material contains a 2-pyrazolin-5-one coupler precursor corresponding to one of the following general formulae I or II:

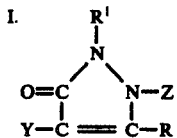 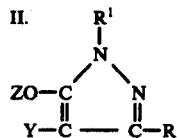

in which $R^1$ represents an alkyl group or an aryl group,

R represents an alkyl group, an aryl group, an anilino group, or an acylamino group derived from a carboxylic or sulphonic acid, Y represents hydrogen, a group that can be split off during the colour development for the formation of colour-forming coloured or colourless 2-pyrazolin-5-one couplers, or a group that cannot be split off for the formation of 2-pyrazolin-5-one competing coupler, and Z represents an acyl group deriving from an organic carboxylic acid, an alkoxy-carbonyl group, an aryloxycarbonyl group, or the group

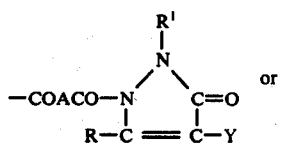

in which $R^1$, R, and Y have the above-defined significance, and A represents an alkylene group or an arylene group.

2. Colour photographic material according to claim 1, wherein the 2-pyrazolin-5-one coupler precursor corresponds to formulae I or II, in which R represents an anilino group or a carboxylic acylamino.

3. Colour photographic material according to claim 1, wherein the fast-acting hardener is a carbamoyl pyridinium hardener corresponding to the following formula:

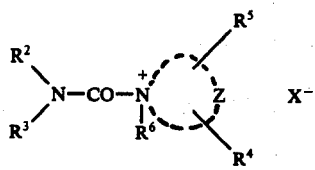

in which $R^2$ represents an alkyl, aryl, or aralkyl group $R^3$ represents (1) an alkyl, aryl, or aralkyl group, and the same meaning as $R^2$, or (2) an alkyl, aryl, aralkyl, or alkylarylalkyl group substituted with a further carbamoylammonium group of the following formula:

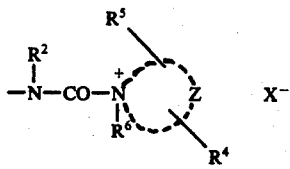

or $R^2$ and $R^3$ together represent the atoms required to complete a heterocyclic ring, $R^4$ represents hydrogen, alkyl, or the group $+A+_a$, in which A represents a vinyl group of a polymerizable vinyl compound or of a copolymer with other copolymerizable monomers and $a$ represents a number such that the molecular weight of the compound is greater than 1000, $R^5$ hydrogen or alkyl or, when Z denotes the atomic group required for completing a pyridinium ring and $R^4$ is absent, $R^5$ denotes a formylamino, acylamino, or ureido group, an alkyl group substituted with acylamino or ureido groups, an amido group, or alkyl, which is substituted with an amido group, a straight chain or branched chain alkyl substituted with hydroxyl, alkyl, formyloxy, acyloxy or a carbamoyloxy, a straight chain or branched chain alkyl substituted with an amino, alkylamino, formylamino, acylamino, or ureido group, $R^6$ represents alkyl, aryl, or aralkyl, but $R^6$ is absent, if the nitrogen atom, to which $R^6$ is attached, carries a double bond in the heterocyclic aromatic ring formed by Z, Z represents the group of atoms required for completing a 5-membered or 6-membered heterocyclic aromatic ring, including a condensed ring system, which group may include 1 or more additional heteroatoms, and X represents an anion.

4. Colour photographic material according to claim 1, wherein the hardener is a carbamoyl pyridinium hardener corresponding to the following general formula:

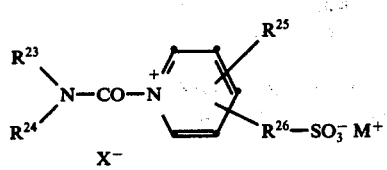

in which $R^{23}$ represents an alkyl, aryl, or aralkyl group,
$R^{24}$ represents
 (1) an alkyl, aryl, or aralkyl group, and the same meaning as $R^{23}$ or
 (2) an alkyl, aryl, aralkyl, or alkylarylalkyl group substituted with a further carbamoylammonium group of the following formula

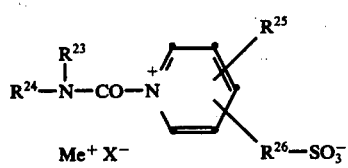

or $R^{23}$ and $R^{24}$ together represent the atoms required to complete a heterocyclic ring $R^{25}$ represents hydrogen, methyl, or ethyl, $R^{26}$ represents methylene, ethylene, propylene, or a simple chemical bond, Me$^+$ represents an alkali metal cation, X$^-$ represents an anion.

5. Colour photographic material according to claim 1, wherein the hardener is a carbamoyl pyridinium hardener corresponding to the following general formula:

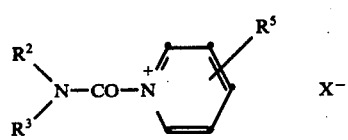

in which $R^2$ represents an alkyl, aryl, or aralkyl group,
$R^3$ represents
 (1) an alkyl, aryl, or aralkyl group, and the same meaning as $R^2$, or
 (2) an alkyl, aryl, aralkyl, or alkylarylalkyl group substituted with a further carbamoylammonium group of the following formula:

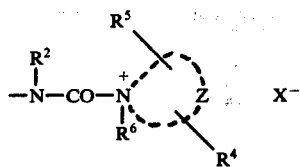

or $R^2$ and $R^3$ together represent the atoms required to complete a heterocyclic ring, X represents an anion, $R^5$ represents hydrogen or one of the following groups:

| | |
|---|---|
| —NR$^7$—CO—R$^8$ | $R^7$ = H, Alkyl (C$_1$—C$_4$) <br> $R^8$ = H, Alkyl (C$_1$—C$_4$), NR$^9$R$^{10}$ <br> $R^9$,R$^{10}$ = (similar or different) H, Alkyl (C$_1$—C$_4$) |
| —(CH$_2$)$_m$—NR$^{11}$R$^{12}$ | $R^{11}$ = —CO—R$^{13}$ <br> $R^{12}$ = H, Alkyl (C$_1$—C$_4$) <br> $R^{13}$ = H, Alkyl (C$_1$—C$_4$), NR$^{14}$R$^{15}$ <br> $R^{14}$ = Alkyl (C$_1$—C$_4$), Aryl <br> $R^{15}$ = H, Alkyl, Aryl <br> m = 1–3 |
| —(CH$_2$)$_n$—CONR$^{16}$R$^{17}$ | $R^{16}$ = H, Alkyl (C$_1$—C$_4$), Aryl <br> $R^{17}$ = H, Alkyl (C$_1$—C$_4$) or <br> $R^{16}$ and $R^{17}$ together represent the atoms required to complete a 5-membered or 6-membered aliphatic ring <br> n = 0–3 |
| —(CH$_2$)$_p$—CH—R$^{18}$ <br>  $\vert$ <br>  Y <br>  $\vert$ <br>  R$^{19}$ | $R^{18}$ = H, Alkyl (C$_1$—C$_4$), which may be substituted by halogen <br> Y = —O—, —NR$^{20}$— <br> $R^{19}$ = H, Alkyl, —CO—R$^{21}$, —CO—NHR$^{22}$ <br> $R^{20}$, $R^{21}$, $R^{22}$ = (similar or different) H, Alkyl (C$_1$—C$_4$) <br> p = 2–3 |

6. Colour photographic material according to claim 1, wherein the hardener is a carbamoyl oxypyridinium hardener corresponding to the general formula:

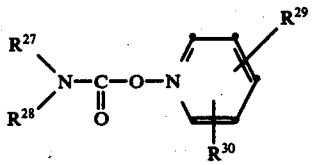

in which $R^{27}$ represents alkyl or aryl $R^{28}$ represents alkyl or the group

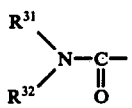

$R^{31}$ represents hydrogen or alkyl, and
$R^{32}$ represents alkyl, $R^{27}$ and $R^{28}$ together represent the atoms required to complete a heterocyclic ring system e.g. a pyrrolidine, morpholine, piperidine, perhydroazepine, 1,2,3,4,-tetrahydroquinoline, or imidazoline-2-OH ring, or $R^{27}$ and $R^{28}$ together represent the atoms required to complete a piperazine ring, in which the second nitrogen atom establishes the connection to a second similar molecular grouping corresponding to the general formulae, $R^{29}$ represents hydrogen halogen, alkyl, oxyalkyl, cyano, —CONH$^2$, or —NH-CO-O-alkyl, $R^{30}$ represents hydrogen or alkyl, X represents an anion.

7. Colour photographic material according to claim 1, wherein the hardener is a carbodiimide hardener corresponding to the following general formula:

$$R^{31}-N=C=N-R^{32}$$

in which:

$R^{31}$ and $R^{32}$ represents (similar or different) alkyl, alkoxyalkyl, an aryl group or a 5-membered heterocyclic ring, or $R^{31}$ represents alkyl having 1 to 5 carbon atoms, and $R^{32}$ represents the group

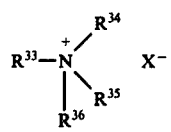

in which $R^{33}$ represents alkyl having 1 to 5 carbon atoms, $R^{34}$ and $R^{35}$ represent alkyl having 1 to 3 carbon atoms, or $R^{34}$ and $R^{35}$ together represent a 6-membered heterocyclic ring having 1 to 2 hetero atoms, $R^{36}$ represents hydrogen or lower alkyl, and X represents an anion.

8. Colour photographic material according to claim 1, wherein the hardener is a dihydroquinoline hardener corresponding to one of the following general formulae:

and

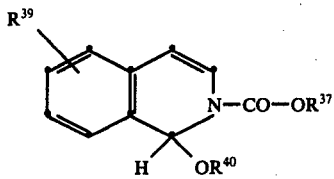

in which $R^{37}$ represents an alkyl group, $R^{38}$ represents an alkyl or aralkyl group, or if $R^{39}$ represents hydrogen, the group

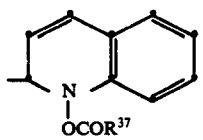

$R^{39}$ represents hydrogen, halogen, alkyl, or alkoxy, and $R^{40}$ represents an alkyl group.

* * * * *